United States Patent
Chernajovsky et al.

(10) Patent No.: US 6,942,853 B2
(45) Date of Patent: Sep. 13, 2005

(54) LATENT FUSION PROTEIN

(75) Inventors: Yuti Chernajovsky, London (GB); Hanna Stina Dreja, Montpellier (FR); Gillian Adams, London (GB)

(73) Assignee: Queen Mary and Westfield College, London (GB)

( * ) Notice: Subject to any disclaimer, the term of this patent is extended or adjusted under 35 U.S.C. 154(b) by 118 days.

(21) Appl. No.: 09/756,283

(22) Filed: Jan. 9, 2001

(65) Prior Publication Data

US 2002/0151478 A1 Oct. 17, 2002

(51) Int. Cl.⁷ .................... A61K 45/00; A61K 39/00; A61K 38/00; C07K 14/00; C07K 17/00

(52) U.S. Cl. .................. 424/85.1; 424/198.1; 530/350; 530/351; 514/2; 435/69.1; 435/69.51

(58) Field of Search ................................ 530/350, 351; 514/2; 435/69.1, 69.51; 424/85.1, 198.1

(56) References Cited

U.S. PATENT DOCUMENTS

| | | | |
|---|---|---|---|
| 5,697,901 A | 12/1997 | Eriksson | 604/46 |
| 5,801,231 A | 9/1998 | Derynck et al. | 536/23.1 |
| 6,080,575 A | 6/2000 | Heidtmann et al. | |
| 6,670,147 B1 | 12/2003 | Heidtmann et al. | |
| 2004/0110682 A1 | 6/2004 | Heidtmann et al. | |

FOREIGN PATENT DOCUMENTS

| | | |
|---|---|---|
| AU | 738717 | 7/1998 |
| CA | 2227159 | 7/1998 |
| EP | 0 373 994 A1 | 6/1990 |
| EP | 0 704 532 A2 | 4/1996 |
| GB | 2 324 960 A | 11/1998 |
| WO | WO 91/08291 A2 | 6/1991 |
| WO | WO 94/26892 A1 | 11/1994 |
| WO | WO 00/20449 A2 | 4/2000 |

OTHER PUBLICATIONS

Renauld, J. 2003. Nature Reviews in Immunology, vol. 3(8), pp. 667–676.*
Opal et al., Chest, 2000, vol. 117, pp. 1162–1172.*
Chernajovsky, Y., et al., "Engineering T cells and molecules for targeting joints and inflammation," *Arthritis Res.* 3(suppl.1):A4, Biomed Central, Ltd. (Apr. 2001).
Baugh, M.D., et al., "Matrix Metalloproteinase Levels Are Elevated in Inflammatory Bowel Disease," *Gastroenterology* 117:814–822, American Gastroenterological Association (1999).
Brunner, A.M., et al., "Site–directed Mutagenesis of Cysteine Residues in the Pro Region of the Transforming Growth Factor β1 Precursor," *J. Biol. Chem.* 264:13660–13664, The American Society for Biochemistry and Molecular Biology, Inc. (1989).
Brunner, A.M., et al., "Site–Directed Mutagenesis of Glycosylation Sites in the Transforming Growth Factor–β1 (TGFβ1) and TGFβ2 (414) Precursors and of Cysteine Residues within Mature TGFβ1: Effects on Secretion and Bioactivity," *Mol. Endocrinol.* 6:1691–1700, The Endocrine Society (1992).
Carroll, M.C., "The Role of Complement and Complement Receptors in Induction and Regulation of Immunity," *Annu. Rev. Immunol.* 16:545–568, Annual Reviews Inc. (1998).
Chernajovsky, Y., et al., "Efficient Constitutive Production of Human Fibroblast Interferon by Hamster Cells Transformed with the IFN–β₁ Gene Fused to An SV40 Early Promoter," *DNA* 3:297–308, Mary Ann Liebert, Inc. (1984).
Chernajovsky, Y., et al., "Pathogenic lymphoid cells engineered to express TGF β1 ameliorate disease in a collagen-induced arthritis model," *Gene Ther.* 4:553–559, Stockton Press (1997).
Coombs, G.H. and Mottram, J.C., "Parasite proteinases and amino acid metabolism: possibilities for chemotherapeutic exploitation," *Parasitology* 114:S61–S80, Cambridge University Press (1997).
Crawford, S.E., et al., "Thrombospondin–1 Is a Major Activator of TGF–β1 In Vivo," *Cell* 93:1159–1170, Cell Press (1998).
DeClerck, Y.A., et al., "Inhibition of Invasion and Metastasis in Cells Transfected with an Inhibitor of Metalloproteinases," *Cancer Res.* 52:701–708, The American Association for Cancer Research (1992).
de Martin, R., et al., "Complementary DNA for human glioblastoma–derived T cell suppressor factor, a novel member of the transforming growth factor–β gene family," *EMBO J.* 6:3673–3677, IRL Press Ltd. (1987).
Derynck, R., et al., "Human transforming growth factor–β complementary DNA sequence and expression in normal and transformed cells," *Nature* 316:701–705, Macmillan Publishers Ltd. (1985).
Derynck, R., et al., "A new type of transforming growth factor–β, TGF–β3," *EMBO J.* 7:3737–3743, IRL Press Ltd. (1988).

(Continued)

Primary Examiner—Janet Andres
(74) Attorney, Agent, or Firm—Sterne Kessler Goldstein & Fox P.L.L.C.

(57) ABSTRACT

This invention provides a nucleic acid construct comprising a first nucleic acid sequence encoding a pharmaceutically active agent and a second nucleotide sequence encoding a latency associated peptide, in which a nucleic acid sequence encoding a proteolytic cleavage site is provided between the first and second nucleic acid sequences. The invention further provides a fusion protein comprising a latency associated peptide and a proteolytic cleavage site wherein the fusion protein is associated with a pharmaceutically active agent. Also disclosed are processes for preparing the construct and fusion protein, methods of treatment using the construct and fusion protein and pharmaceutical compositions containing the construct and fusion protein.

23 Claims, 17 Drawing Sheets

OTHER PUBLICATIONS

Derynck, R., "TGF-β–receptor–mediated signaling," *Trends in Biochem. Sci.* 19:548–553, Elsevier Science Ltd. (1994).

Dreja, H., et al., "Soluble Complement Receptor 1 (CD35) Delivered by Retrovirally Infected Syngeneic Cells or by Naked DNA Injection Prevents the Progression of Collagen–Induced Arthritis," *Arthritis & Rheumatism* 43:1698–1709, American College of Rheumatology (Aug. 2000).

Eklöv, S., et al., "Lack of the Latent Transforming Growth Factor β Binding Protein in Malignant, but not Benign Prostatic Tissue," *Cancer Res.* 53:3193–3197, American Association for Cancer Research (1993).

Gibson, M.A., "Bovine Latent Transforming Growth Factgor β1–Binding Protein 2: Molecular Cloning, Identification of Tissue Isoforms, and Immunolocalization to Elastin–Associated Microfibrils," *Molec. Cell. Biol.* 15:6932–6942, American Society for Microbiology (1995).

Goldman, M.H., et al., "Monitoring proteolysis of recombinant human interferon–γ during batch culture of Chinese hamster ovary cells," *Cytotechnol.* 23:103–111, Kluwer Academic Publishers (1997).

Gordon, E.M., et al., "Capture and Expansion of Bone Marrow–Derived Mesenchymal Progenitor Cells with a Transforming Growth Factor–β1—von Willebrand's Factor fusion Protein for Retrovirus–Mediated Delivery of Coagulation Factor IX," *Hum. Gene Ther.* 8:1385–1394, Mary Ann Liebert, Inc. (1997).

Han, Z., et al., "AP–1 and NF–κB Regulation in Rheumatoid Arthritis and Murine Collagen–Induced Arthritis," *Autoimmunity* 28:197–208, Harwood Academic Publishers (1998).

Hanks, S.K., "Amino acid sequence of the BSC–1 cell growth inhibitor (polyergin) deduced from the nucleotide sequence of the cDNA," *Proc. Natl. Acad. Sci. USA* 85:79–82, National Academy of Sciences of the USA (1988).

Iwakura, Y., et al., "Purification of Mouse L Cell Interferon," *J. Biol. Chem.* 253:5074–5079, The American Society of Biological Chemists, Inc. (1978).

Jakowlew, S.B., et al., "Complementary Deoxyribonucleic Acid Cloning of a Messenger Ribonucleic Acid Encoding Transforming Growth Factor β 4 from Chicken Embryo Chondrocytes," *Molec. Endocrinol.* 2:1186–1195, The Endocrine Society (1988).

Janssens, K., et al., "Mutations in the gene encoding the latency–associated peptide of TGF–β1 cause Camurati–Engelmann disease,"*Nature Genetics* 26:273–275, Macmillan Magazines Ltd. (Nov. 2000).

Kanzaki, T., et al., "TGF–β1 Binding Protein: A component of the Large Latent Complex of TGF–β1 with Multiple Repeat Sequences," *Cell* 61:1051–1061, Cell Press (1990).

Khalil, N., "TGF–β: from latent to active," *Microbes and Infection* 1:1255–1263, Elsevier (1999).

Kojima, S., et al., "Requirement for Transglutaminase in the Activation of Latent Transforming Growth Factor–β in Bovine Endothelial Cells," *J. Cell Biol.* 121:439–448, The Rockefeller University Press (1993).

Kondaiah, P., et al., "Identification of a Novel Transforming Growth Factor–β (TGF–β5) mRNA in *Xenopus laevis*," *J. Biol. Chem.* 265:1089–1093, The American Society for Biochemistry and Molecular Biology, Inc. (1990).

Kubota, E., et al., "Interleukin 1β and Stromelysin (MMP3) Activity of Synovial Fluid as Possible Markers of Osteoarthritis in the Temporomandibular Joint," *J. Oral Maxillofac. Surg.* 55:20–27, American Association of Oral and Maxillofacial Surgery (1997).

Leppert, D., et al., "Matrix metalloproteinase–9 (gelatinase B) is selectively elevated in CSF during relapses and stable phases of multiple sclerosis," *Brain* 121:2327–2334, Oxford University Press (1998).

Libby, P., "The interfce of atherosclerosis and thrombosis: basic mechanisms," *Vasc. Med.* 3:225–229, Arnold (1998).

Lode, H.N., et al., "Immunocytokines: A Promising Approach to Cancer Immunotherapy," *Pharmacol. Ther.* 80:277–292, Elsevier Science Inc. (1998).

Louis, E., et al., "Increased production of matrix metalloproteinase–3 and tissue inhibitor of metalloproteinase–1 by inflamed mucosa in inflammatory bowel disease," *Clin. Exp. Immunol.* 120:241–246, Blackwell Science (May 2000).

Massova, I., et al., "Structural Insights into the Catalytic Domains of Human Matrix Metalloprotease–2 and Human Matrix Metalloprotease–9: Implications for Substrate Specificities," *J. Mol. Model.* 3:17–30, Springer–Verlag (1997).

Masure, S., et al., "Production and characterization of recombinant active mouse gelatinase B from eukaryotic cells and in vivo effects after intravenous administration," *Eur. J. Biochem.* 244:21–30, Springer International (1997).

McKerrow, J.H., "Development of cysteine protease inhibitors as chemotherapy for parasitic diseases: insights on safety, target validation, and mechanism of action," *Intl. J. Parasitol.* 29:833–837, Elsevier Science Ltd. (1999).

Miyazono, K., et al., "A role of the latent TGF–β1 binding protein in the assembly and secretion of TGF–β1," *EMBO J.* 10:1091–1101, Oxford University Press (1991).

Miyazono, K., et al., "Retention of the Transforming Growth Factor–β1 Precursor in the Golgi Complex in a Latent Endoglycosidase H–sensitive Form," *J. Biol. Chem.* 267:5668–5675, The American Society for Biochemistry and Molecular Biology, Inc. (1992).

Morén, A., et al., "Identification and Characterization of LTBP–2, a Novel Latent Transforming Growth Factor–β–binding Protein," *J. Biol. Chem.* 269:32469–32478, The American Society for Biochemistry and Molecular Biology, Inc. (1994).

Munger, J.S., et al., "Interactions between Growth Factors and Integrins: Latent Forms of Transforming Growth Factor–β Are Ligands for Integrin αvβ1," *Molec. Biol. Cell* 9:2627–2638, The American Society for Cell Biology (1998).

Nagase, H., and Fields, G.B., "Human Matrix Metalloproteinase Specificity Studies Using Collagen Sequence–Based Synthetic Peptides," *Biopolymers* (*Peptide Sci.*) 40:399–416, Wiley–Interscience (1996).

Nunes, I., et al. "Latent Transforming Growth Factor–β Binding Protein Domains Involved in Activation and Transflutaminase–dependent Cross–Linking of Latent Transforming Growth Factor–β" *J. Cell. Biol.* 136:1151–1163, The Rockefeller University Press (1997).

Ogata, Y., et al., "Steps Involved in Activation of the Pro–matrix Metalloproteinase 9 (Progelatinase B)–Tissue Inhibitor of Metalloproteinases–1 Complex by 4–Aminophenylmercuric Acetate and Proteinases," *J. Biol. Chem.* 270:18506–18511, The American Society for Biochemistry and Molecular Biology, Inc. (1995).

Peng, K.-W., et al., "A Gene Delivery System Activatable by Disease–Associated Matrix Metalloproteinases," *Hum. Gene Ther.* 8:729–738, Mary Ann Liebert, Inc. (1997).

Roberts, A.B., and Sporn, M.B., "Chapter 8. The Transforming Growth Factor–βs," in *Peptide Growth Factors and Their Receptors I*, Sporn, M.B. and Roberts, A.B., eds., Springer–Verlag, Berlin, Germany, pp. 419–472 (1990).

Roth–Eichhorn, S., et al., "Subcellular Localization of (Latent) Transforming Growth Factor β and the Latent TGF–β Binding Protein in Rat Hepatocytes and Hepatic Stellate Cells," *Hepatology* 28:1588–1596, W.B. Saunders Co. (1998).

Saharinen, J., et al., "Identification and Characterization of a New Latent Transforming Growth Factor–β–binding Protein, LTBP–4," *J. Biol. Chem.* 273:18459–18469, The American Society for Biochemistry and Molecular Biology, Inc. (1998).

Saharinen, J., et al., "Latent transforming growth factor–β binding proteins (LTBPs)—structural extracellular matrix proteins for targeting TGF–β action," *Cytokines & Growth Factor Rev.* 10:99–117, Elsevier Science Ltd. (1999).

Sanderson, N., et al., "Hepatic expression of mature transforming growth factor β1 in transgenic mice results in multiple tissue lesions," *Proc. Natl. Acad. Sci. USA* 92:2572–2576, National Academy of Sciences of the USA (1995).

Saharinen, J., et al., "Association of the small latent transforming growth factor–β with an eight cysteine repeat of its binding protein LTBP–1," *EMBO J.* 15:245–253, Oxford University Press (1996).

Satoh, M., et al., "Stable production of recombinant pro–urokinase by human lymphoblastoid Namalwa KJM–1 cells: Host–cell dependency of the expressed–protein stability," *Cytotechnology* 13:79–88, Kluwer Academic Publishers (1993).

Schultz–Cherry, S., et al., "The Type 1 Repeats of Thrombospondin 1 Activate Latent Transforming Growth Factor–β," *J. Biol. Chem.* 269:26783–26788, The American Society for Biochemistry and Molecular Biology, Inc. (1994).

Singer, I.I., et al., "Aggrecanase and metalloproteinase–specific aggrecan neo–epitopes are induced in the articular cartilage of mice with collagen II–induced arthritis," *Osteoarthritis and Cartilage* 5:407–418, WB Saunders Ltd. (1997).

Tsuji, T., et al., "Molecular cloning of the large subunit of transforming growth factor type β masking protein and expression of the mRNA in various rat tissues," *Proc. Natl. Acad. Sci. USA* 87:8835–8839, National Academy of Sciences of the USA (1990).

ten Dijke, P., et al. "Identification of another member of the transforming growth factor type β gene family," *Proc. Natl. Acad. Sci USA* 85:4715–4719, National Academy of Sciences of the USA (1988).

Tort, J., et al., "Proteinases and Associated Genes of Parasitic Helminths," *Adv. Parasitol.* 43:161–266, Academic Press (1999).

Triantaphyllopoulos, K.A., et al., "Cloning and expression of muring IFNβ and a TNF antagonist for gene therapy of experimental allergic encephalomyelitis," *Gene Ther.* 5:253–263, Stockton Press (1998).

Uhlmann, E., "Peptide Nucleic Acids (PNA) and PNA–DNA Chimeras: From High Binding Affinity towards Biological Function," *Biol. Chem.* 379:1045–1052, Walter de Gruyter (1998).

Uhm, J.H., et al., "Migratory Behavior of Lymphocytes Isolated from Multiple Sclerosis Patients: Effects of Interferon β–1b Therapy," *Ann. Neurol.* 46:319–324, American Neurological Association (1999).

van Meurs, J., et al., "Cleavage of Aggrecan at the $Asn^{341}$–$Phe^{342}$ Site Coincides With the Initiation of Collagen Damage in Murine Antigen–Induced Arthritis," *Arthritis & Rheumat.* 42:2074–2084, American College of Rheumatology (1999).

Vodovotz, Y., et al., "Regulation of Transforming Growth Factor β1 by Nitric Oxide," *Cancer Res.* 59:2142–2148, American Association for Cancer Research (1999).

Voth, B.R., et al., "Differentially expressed *Leishmania major gp63* genes encode cell surface leishmanolysin with distinct signals for glycosylphosphatidylinositol attachment," *Molec. Biochem. Parasitol.* 93:31–41, Elsevier Science B.V. (1998).

Vu, T.H., and Werb, Zena, "Matrix metalloproteinases: effectors of development and normal physiology," *Genes & Develop.* 14:2123–2133, Cold Spring Harbor Laboratory Press (Sep. 2000).

Wakefield, L.M., et al., "Recombinant TGF–β1 Is Synthesized as a Two–Component Latent Complex That Shares Some Structural Features with the Native Platelet Latent TFG–β1 Complex," *Growth Factors* 1:203–218, Harwood Academic Publishers GbmH (1989).

Wakefield, L.M., et al., "Recombinant Latent Transforming Growth Factor β1 Has a Longer Plasma Half–Life in Rats than Active Transforming Growth Factor β1, and a Different Tissue Distribution," *J. Clin. Invest.* 86:1976–1984, The Rockefeller University Press (1990).

Williams, L.W., et al., "Complement: function and clinical relevance," *Ann. Allergy* 60:293–302, American College of Allergy and Immunology (1988).

Wyman, T.B., et al., "Design, Synthesis, and Characterization of a Cationic Peptide That Binds to Nucleic Acids and Permeabilizes Bilayers," *Biochem.* 36:3008–3017, American Chemical Society (1997).

Ye, Q.–Z., et al., "Reconstructed 19 kDa Catalytic Domain of Gelatinase A Is an Active Proteinase," *Biochem.* 34:4702–4708, American Chemical Society (1995).

Yin, W., et al., "Isolation of a Novel Latent Transforming Growth Factor–β Binding Protein Gene (LTBP–3)," *J. Biol. Chem.* 270:10147–10160, The American Society for Biochemistry and Molecular Biology, Inc. (1995).

Yoshioka, M., et al., "Effect of proteases from *Porphyromonas gingivalis* on adhesion molecules of human periodontal ligament fibroblast cells," *Folia Pharmacol. Jpn.* 110:347–355, The Japanese Pharmacological Society (1997).

Young, A.R., et al., "Biochemical aspects of egg hatch in endo– and ectoparasites: potential for rational drug design," *Intl. J. Parasitol.* 29:861–867, Elsevier Science Ltd. (1999).

Yu, Q. and Stamenkovic, I., "Cell surface–localized matrix metalloproteinase–9 proteolytically activates TGF–β and promotes tumor invasive and angiogenesis," *Genes & Develop.* 14:163–176, Cold Spring Harbor Laboratory Press (Jan. 2000).

Zhang, Y., et al., "Molecular Characterization of a Protease Secreted by *Erwinia amylovora*," *J. Mol. Biol.* 289:1239–1251, Academic Press (1999).

\* cited by examiner

TGFb+MMP+ifn b Sequence

| 10 | 20 | 30 | 40 | 50 | 60 | |
|---|---|---|---|---|---|---|
| 1234567890 | 1234567890 | 1234567890 | 1234567890 | 1234567890 | 1234567890 | |
| ATGCCGCCCT | CCGGGCTGCG | GCTGCTGCCG | CTGCTGCTAC | CGCTGCTGTG | GCTACTGGTG | 60 |
| MetProProS | erGlyLeuAr | gLeuLeuPro | LeuLeuLeuP | roLeuLeuTr | pLeuLeuVal | |
| CTGACGCCTG | GCCCGCCGGC | CGCGGGACTA | TCCACCTGCA | AGACTATCGA | CATGGAGCTG | 120 |
| LeuThrProG | lyProProAl | aAlaGlyLeu | SerThrCysL | ysThrIleAs | pMetGluLeu | |
| GTGAAGCGGA | AGCGCATCGA | GGCCATCCGC | GGCCAGATCC | TGTCCAAGCT | GCGGCTCGCC | 180 |
| ValLysArgL | ysArgIleGl | uAlaIleArg | GlyGlnIleL | euSerLysLe | uArgLeuAla | |
| AGCCCCCCGA | GCCAGGGGGA | GGTGCCGCCC | GGCCCGCTGC | CCGAGGCCGT | GCTCGCCCTG | 240 |
| SerProProS | erGlnGlyGl | uValProPro | GlyProLeuP | roGluAlaVa | lLeuAlaLeu | |
| TACAACAGCA | CCCGCGACCG | GGTGGCCGGG | GAGAGTGCAG | AACCGGAGCC | CGAGCCTGAG | 300 |
| TyrAsnSerT | hrArgAspAr | gValAlaGly | GluSerAlaG | luProGluPr | oGluProGlu | |
| GCCGACTACT | ACGCCAAGGA | GGTCACCCGC | GTGCTAATGG | TGGAAACCCA | CAACGAAATC | 360 |
| AlaAspTyrT | yrAlaLysGl | uValThrArg | ValLeuMetV | alGluThrHi | sAsnGluIle | |
| TATGACAAGT | TCAAGCAGAG | TACACACAGC | ATATATATGT | TCTTCAACAC | ATCAGAGCTC | 420 |
| TyrAspLysP | heLysGlnSe | rThrHisSer | IleTyrMetP | hePheAsnTh | rSerGluLeu | |
| CGAGAAGCGG | TACCTGAACC | CGTGTTGCTC | TCCCGGGCAG | AGCTGCGTCT | GCTGAGGAGG | 480 |
| ArgGluAlaV | alProGluPr | oValLeuLeu | SerArgAlaG | luLeuArgLe | uLeuArgArg | |
| CTCAAGTTAA | AAGTGGAGCA | GCACGTGGAG | CTGTACCAGA | AATACAGCAA | CAATTCCTGG | 540 |
| LeuLysLeuL | ysValGluGl | nHisValGlu | LeuTyrGlnL | ysTyrSerAs | nAsnSerTrp | |
| CGATACCTCA | GCAACCGGCT | GCTGGCACCC | AGCGACTCGC | CAGAGTGGTT | ATCTTTTGAT | 600 |
| ArgTyrLeuS | erAsnArgLe | uLeuAlaPro | SerAspSerP | roGluTrpLe | uSerPheAsp | |
| GTCACCGGAG | TTGTGCGGCA | GTGGTTGAGC | CGTGGAGGGG | AAAATTGAGGG | CTTTCGCCTT | 660 |
| ValThrGlyV | alValArgGl | nTrpLeuSer | ArgGlyGlyG | luIleGluGl | yPheArgLeu | |
| AGCGCCCACT | GCTCCTGTGA | CAGCAGGGAT | AACACACTGC | AAGTGGACAT | CAACGGGTTC | 720 |
| SerAlaHisC | ysSerCysAs | pSerArgAsp | AsnThrLeuG | lnValAspIl | eAsnGlyPhe | |

FIG. 1A

```
ACTACCGGCC GCCGAGGTGA CCTGGCCACC ATTCATGGCA TGAACCGGCC TTTCCTGCTT    780
ThrThrGlyA rgArgGlyAs pLeuAlaThr IleHisGlyM etAsnArgPr oPheLeuLeu

CTCATGGCCA CCCCGCTGGA GAGGGCCCAG CATCTGCAAA GCGAATTCGG GGGAGGCGGA    840
LeuMetAlaT hrProLeuGl uArgAlaGln HisLeuGlnS erGluPheGl yGlyGlyGly

TCCCCGCTCG GGCTTTGGGC GGGAGGGGGC TCAGCGGCCG CAATCAACTA TAAGCAGCTC    900
SerProLeuG lyLeuTrpAl aGlyGlyGly SerAlaAlaA laIleAsnTy rLysGlnLeu

CAGCTCCAAG AAAGGACGAA CATTCGGAAA TGTCAGGAGC TCCTGGAGCA GCTGAATGGA    960
GlnLeuGlnG luArgThrAs nIleArgLys CysGlnGluL euLeuGluGl nLeuAsnGly

AAGATCAACC TCACCTACAG GGCGGACTTC AAGATCCCTA TGGAGATGAC GGAGAAGATG    1020
LysIleAsnL euThrTyrAr gAlaAspPhe LysIleProM etGluMetTh rGluLysMet

CAGAAGAGTT ACACTGCCTT TGCCATCCAA GAGATGCTCC AGAATGTCTT TCTTGTCTTC    1080
GlnLysSerT yrThrAlaPh eAlaIleGln GluMetLeuG lnAsnValPh eLeuValPhe

AGAAACAATT TCTCCAGCAC TGGGTGGAAT GAGACTATTG TTGTACGTCT CCTGGATGAA    1140
ArgAsnAsnP heSerSerTh rGlyTrpAsn GluThrIleV alValArgLe uLeuAspGlu

CTCCACCAGC AGACAGTGTT TCTGAAGACA GTACTAGAGG AAAAGCAAGA GGAAAGATTG    1200
LeuHisGlnG lnThrValPh eLeuLysThr ValLeuGluG luLysGlnGl uGluArgLeu

ACGTGGGAGA TGTCCTCAAC TGCTCTCCAC TTGAAGAGCT ATTACTGGAG GGTGCAAAGG    1260
ThrTrpGluM etSerSerTh rAlaLeuHis LeuLysSerT yrTyrTrpAr gValGlnArg

TACCTTAAAC TCATGAAGTA CAACAGCTAC GCCTGGATGG TGGTCCGAGC AGAGATCTTC    1320
TyrLeuLysL euMetLysTy rAsnSerTyr AlaTrpMetV alValArgAl aGluIlePhe

AGGAACTTTC TCATCATTCG AAGACTTACC AGAAACTTCC AAAACTGATC TAGACC        1376
ArgAsnPheL euIleIleAr gArgLeuThr ArgAsnPheG lnAsn***Se rArg
                                                  uga
```

FIG. 1B ifn+MMP+TGFb Sequence

| | | | | | | |
|---|---|---|---|---|---|---|
| 10 | 20 | 30 | 40 | 50 | 60 | |
| 1234567890 | 1234567890 | 1234567890 | 1234567890 | 1234567890 | 1234567890 | |
| ATGAACAACA | GGTGGATCCT | CCACGCTGCG | TTCCTGCTGT | GCTTCTCCAC | CACAGCCCTG | 60 |
| MetAsnAsnA | rgTrpIleLe | uHisAlaAla | PheLeuLeuC | ysPheSerTh | rThrAlaLeu | |
| TCCATCAACT | ATAAGCAGCT | CCAGCTCCAA | GAAAGGACGA | ACATTCGGAA | ATGTCAGGAG | 120 |
| SerIleAsnT | yrLysGlnLe | uGlnLeuGln | GluArgThrA | snIleArgLy | sCysGlnGlu | |
| CTCCTGGAGC | AGCTGAATGG | AAAGATCAAC | CTCACCTACA | GGGCGGACTT | CAAGATCCCT | 180 |
| LeuLeuGluG | lnLeuAsnGl | yLysIleAsn | LeuThrTyrA | rgAlaAspPh | eLysIlePro | |
| ATGGAGATGA | CGGAGAAGAT | GCAGAAGAGT | TACACTGCCT | TTGCCATCCA | AGAGATGCTC | 240 |
| MetGluMetT | hrGluLysMe | tGlnLysSer | TyrThrAlaP | heAlaIleGl | nGluMetLeu | |
| CAGAATGTCT | TTCTTGTCTT | CAGAAACAAT | TTCTCCAGCA | CTGGGTGGAR | TGAGACTATT | 300 |
| GlnAsnValP | heLeuValPh | eArgAsnAsn | PheSerSerT | hrGlyTrpAs | nGluThrIle | |
| GTTGTACGTC | TCCTGGATGA | ACTCCACCAG | CAGACAGTGT | TTCTGAAGAC | AGTACTAGAG | 360 |
| ValValArgL | euLeuAspGl | uLeuHisGln | GlnThrValP | heLeuLysTh | rValLeuGlu | |
| GAAAAGCAAG | AGGAAAGATT | GACGTGGGAG | ATGTCCTCAA | CTGCTCTCCA | CTTGAAGAGC | 420 |
| GluLysGlnG | luGluArgLe | uThrTrpGlu | MetSerSerT | hrAlaLeuHi | sLeuLysSer | |
| TATTACTGGA | GGGTGCAAAG | GTACCTTAAA | CTCATGAAGT | ACAACAGCTA | CGCCTGGATG | 480 |
| TyrTyrTrpA | rgValGlnAr | gTyrLeuLys | LeuMetLysT | yrAsnSerTy | rAlaTrpMet | |
| GTGGTCCGAG | CAGAGATCTT | CAGGAACTTT | CTCATCATTC | GAAGACTTAC | CAGAAACTTC | 540 |
| ValValArgA | laGluIlePh | eArgAsnPhe | LeuIleIleA | rgArgLeuTh | rArgAsnPhe | |
| CAAAACGAAT | TCGGGGAGG | CGGATCCCCG | CTCGGGCTTT | GGGCGGGAGG | GGGCTCAGCG | 600 |
| GlnAsnGluP | heGlyGlyGl | yGlySerPro | LeuGlyLeuT | rpAlaGlyGl | yGlySerAla | |
| GCCGCACTAT | CCACCTGCAA | GACTATCGAC | ATGGAGCTGG | TGAAGCGGAA | GCGCATCGAG | 660 |
| AlaAlaLeuS | erThrCysLy | sThrIleAsp | MetGluLeuV | alLysArgLy | sArgIleGlu | |
| GCCATCCGCG | GCCAGATCCT | GTCCAAGCTG | CGGCTCGCCA | GCCCCCCGAG | CCAGGGGGAG | 720 |
| AlaIleArgG | lyGlnIleLe | uSerLysLeu | ArgLeuSlaS | erProProSe | rGlnGlyGlu | |

FIG.2A

```
GTGCCGCCCG GCCCGCTGCC CGAGGCCGTG CTCGCCCTGT ACAACAGCAC CCGCGACCGG     780
ValProProG lyProLeuPr oGluAlaVal LeuAlaLeuT yrASnSerTh rArgAspArg

GTGGCCGGGG AGAGTGCAGA ACCGGAGCCC GAGCCTGAGG CCGACTACTA CGCCAAGGAG     840
ValAlaGlyG luSerAlaGl uProGluPro GluProGluA laAspTyrTy rAlaLysGlu

GTCACCCGCG TGCTAATGGT GGAAACCCAC AACGAAATCT ATGACAAGTT CAAGCAGAGT     900
ValThrArgV alLeuMetVa lGluThrHis AsnGluIleT yrAspLysPh eLysGlnSer

ACACACAGCA TATATATGTT CTTCAACACA TCAGAGCTCC GAGAAGCGGT ACCTGAACCC     960
ThrHisSerI leTyrMetPh ePheAsnThr SerGluLeuA rgGluAlaVa lProGluPro

GTGTTGCTCT CCCGGGCACA GCTGCGTCTG CTGAGGAGGC TCAAGTTAAA AGTGGAGCAG    1020
ValLeuLeuS erArgAlaGl uLeuArgLeu LeuArgArgL euLysLeuLy sValGluGln

CACGTGGAGC TGTACCAGAA ATACAGCAAC AATTCCTGGC GATACCTCAG CAACCGGCTG    1080
HisValGluL euTyrGlnLy sTyrSerAsn AsnSerTrpA rgTyrheuSe rAsnArgLeu CTGGCACCCA GCGACTCGCC AGAGTGGTTA TCTTTTGATG TCACCGGAGT TGTGCGGCAG    1140
LeuAlaProS erAspSerPr oGluTrpLeu SerPheAspV alThrGlyVa lValArgGln TGGTTGAGCC GTGGAGGGGA AATTGAGGGC TTTCGCCTTA GCGCCCACTG CTCCTGTGAC    1200
TrpLeuSerA rgGlyGlyGl uIleGluGly PheArgheuS erAlaHisCy sSerCysAsp AGCAGGGATA ACACACTGCA AGTGGACATC AACGGGTTCA CTACCGGCCG CCGAGGTGAC    1260
SerArgAspA snThrLeuGl nValAspIle AsnGlyPheT hrThrGlyAr GArgGlyAsp CTGGCCACCA TTCATGGCAT GAACCGGCCT TTCCTGCTTC TCATGGCCAC CCCGCTGGAG    1320
LeuAlaThrI leHisGlyMe tAsnArgPro PheheuLeuL euMetAlaTh rProLeuGlu AGGGCCCAGC ATCTGCAAAG GtgaTCTAGA CC                                  1352
ArgAlaGlnH isLeuGlnSe r...SerArg
```

FIG.2B

```
                   1                    20                       40                           60
Hu TGF-β   1  MPPSGLRLLPLLPLLWLLV-LTPGPPAAGLSTCKTIOMELVKRKRIEAIRGQILSKLRLASPPSQGE-VP-PGP
Hu TGF-β   2  MHYCVLSAFLILH    LVTVAL-------SLSTCSTLDMQFMRKRIEAIRGQILSKLKLTSPP---EDYPEPEE
Hu TGF-β   3  MKMHLQRALVVLALLHFATVSL--------SLSTCTTLDFGHIKKKRVEAIRGQILSKLRLTSPP---EPTV-MTH
Ck TGF-β   4  ...........................
Fg TGF-β   5  MEV--------LWMLLVLLV-LHLSSLANSLSTCKAVDMEEVRKRRIEAIRGQILSKLKLDKIPDVDS-EK-MTV
                                +           +          +++*          + ++++++++++ + +

80                      100                     120
Hu TGF-β   1  LPEAVLALYNSTRDRVAGESAEPE-PEP-------EADYAKEVIRVLMV----ETHNEIYDKFKQSTHSIYMFF
Hu TGF-β   2  VPPEVISIYNSTRDLL--QEKASR-RAAACERERSOEEYYAKEVYKIDMPPFFPS-ENAIPPTFYRPY-FRIVRF
Hu TGF-β   3  VPYQVLALYNSTRELL--EEHGER-KEEGCTQENTESEYYAKEIHKFDMIQGLAE-HNELAVCPKGIT-SKVFRF
Ck TGF-β   4  ------------------M--DPMSIGPK--SCG----------------------GSPW-RPP-GTAPWSIG-SR--RA
Fg TGF-β   5  PSEAIF-LYNSTLE-VIREKATRE-EEEHVGHDONIQDYYAKQVYRF-----ESITELEDHEFKFK--------F
                   +++                              ++++

140                      160                       180
Hu TGF-β   1  NTSEL------RE-AVPEPVLLS-RAELRLLRLKL----KV-EQHVELYQ-----KYSNNSWRYLSNRLLAPSDSPE
Hu TGF-β   2  DVSA--------MEKNASNLV-KAEFRVFRLQNPK-ARVPEQRIELYQILKSKDLISPTQRYIDSKVVKTRAEGE
Hu TGF-β   3  NVSS--------VEKNRTNLF-RAEFRVLRVPNPS-SKRNEQRIELFQILRP-DEHIAKQRYIGGKNLPTRGTAE
Ck TGF-β   4  TASSSCSTSSRVRAEVGGRALLHRAELRHLRQKAAADSAGTEQRLELYQGYG----NASWRYLHGRSVRATADDE
Fg TGF-β   5  NASHV------RENVGMN-SLLH-HAELRMYK-KQTD--KNMOQRMELFW--KYQENGTTHSRYLESKYITPVTDQE
                   +            +           +            +         ++           +
```

FIG.3A

```
                     200                      220                       240
Hu TGF-β    1   WLSFDVTGVVRQWLSRGGEIEGFRLSAHCSG-------DSRDNTLQVDIN-GFTTGR------RGDLATI-----
Hu TGF-β    2   WLSFDVTDAVHEWLHHKDRWLGFKISLHCPCCTFVPSNNYIIPNKSEELEARFA-GIDGTSTYTSGDQKTIKSTRK
Hu TGF-β    3   WLSFDVTDTVREWLLRRESNLGLEISIHCPCHTFQP-NGDILENIHEVMEIKFK-GVDNEDDHGRGDLGRLK---K
Ck TGF-β    4   WLSFDVTDAVHQWLSGSELIGVFKLSVHCPCEMGPG-HADEMRISIEGFEOQ-----------RGDMQSIA---K
Fg TGF-β    5   WNSFDVTKTVNEWLKRAEENEQFGLQPAGKG---------PTPQAKD-----IDIEGFPAL-RGDLASL--SSK
                + +++++ +  ++                                             *  *                  ++

260                  ↓280                      300
Hu TGF-β    1   ---HGMWRPFLLLMATPLERA-QK--LQSS---RHRRALDTNYCFSST--EKNCCVRQLYIDFRKDLGWKWIHEP
Hu TGF-β    2   KNSGKT---PHLLLMLLPSYRL-ESQ----QTNRRKKRALDAAYCFRNV--QDNCCLRPLYIDFKRDLGWKWIHEP
Hu TGF-β    3   QKDNN--N-PHLILMIPPHRL-DNPGQGGQ---RKKRALDTNYCFRNL--EENCCVRPLYIDFRQDLGWKWVHEP
Ck TGF-β    4   -KHRR--V-PYVLAMALPAERANE--LHSA---RRRROLDTDYCFGPGTDEKNCCVRPLYIDFRKDLQWKKWIHEP
Fg TGF-β    5   ENT-----KPYL--MITSMPAERIDTVT SS---RKKRGVGQEYCFGNN-GPNCCVKPLYINFRKDLGWKWIHEP
                                           +       +   +**  +  +++  +     ++  +++  +++   +++

320              340                  360           380        390
Hu TGF-β    1   KGYHANFCLGPCPYIWSLDTQYSKVLALYNQHNPGASAAPCCVPQALEPLPIVYYVGRKPKVEQLSNMIVRSCKCS
Hu TGF-β    2   KGYNANFCAGACPYLWSSDTQHSRVLSLYNTINPEASASPCCVSQDLEPLTILYYIGKIPKIEQLSNMIVKSCKCS
Hu TGF-β    3   KGYYANFCSGPCPYLRSADTTHSTVLGLYNTLNPEASASPCCVPQDLEPLTILYYVGRIPKVEQLSNMVVKSCKCS
Ck TGF-β    4   KGYMANFCMGPCPYIWSADTQYIKVLALYNQHNPGASAAPCCVPQILDPLPLIYYVGRNVRVEQLSNMVVRACKCS
Fg TGF-β    5   KGYEANYCLGNCPYIWSMDTQYSKVLSLYNQHNPGASISPCCVPDVLEPLPLIYYVGRIAKVEQLSNMVVRSCNCS
                +++ ++ + * * ++ +  + +++   ++ +*** ++  +**  +    **   +++++++ +  * ** * *+
```

FIG.3B

| Protein | Sequence | Reference |
|---|---|---|
| MMP-1/MMP-8 | | |
| Human type I collagen (α1) | Ala-Pro-Gln-Gly$_{775}$~Ile$_{776}$-Ala-Gly-Gln | 80 |
| Human type I collagen (α2) | Gly-Pro-Gln-Gly$_{775}$~Leu$_{776}$-Leu-Gly-Ala | 80 |
| Human type II collagen | Gly-Pro-Gln-Gly$_{775}$~Leu$_{776}$-Ala-Gly-Gln | 80 |
| Human type III collagen | Gly-Pro-Leu-Gly$_{775}$~Ile$_{776}$-Ala-Gly-Ile | 80 |
| Human α$_2$-macroglobulin | Gly-Pro-Glu-Gly$_{679}$~Leu$_{680}$-Arg-Val-Gly | 84 |
| Rat α$_2$-macroglobulin | Ala-Ala-Tyr-His$_{681}$~Leu$_{682}$-Val-Ser-Gln | 84 |
| Rat α$_2$-macroglobulin | Met-Asp-Ala-Phe$_{691}$~Leu$_{692}$-Glu-Ser-Ser | 84 |
| Rat α$_1$-macroglobulin | Glu-Pro-Gln-Ala$_{683}$~Leu$_{684}$-Ala-Met-Ser | 84 |
| Rat α$_1$-macroglobulin | Gln-Ala-Leu-Ala$_{685}$~Met$_{686}$-Ser-Ala-Ile | 84 |
| Chicken ovostatin | Pro-Ser-Tyr-Phe$_{673}$~Leu$_{674}$-Asn-Ala-Gly | 79 |
| Human pregnancy zone protein | Tyr-Glu-Ala-Gly$_{685}$~Leu$_{686}$-Gly-Val-Val | 84 |
| Human pregnancy zone protein | Ala-Gly-Leu-Gly$_{687}$~Val$_{688}$-Val-Glu-Arg | 84 |
| Human pregnancy zone protein | Ala-Gly-Leu-Gly$_{757}$~Ile$_{758}$-Ser-Ser-Thr | 84 |
| α$_1$-protease inhibitor | Gly-Ala-Met-Phe$_{352}$~Leu$_{353}$-Glu-Ala-Il | 85 |
| Human aggrecan | Ile-Pro-Glu-Asn$_{341}$~Phe$_{342}$-Phe-Gly-Val | 86 |
| Human aggrecan | Thr-Glu-Gly-Glu$_{373}$~Ala$_{374}$-Arg-Gly-Ser | 86 |
| Human cartilage link | Arg-Ala-Ile-His$_{16}$~Ile$_{17}$-Gln-Ala-Glu | 87 |
| Human insulin-like growth factor binding protein-3 | Leu-Arg-Ala-Tyr$_{99}$~Leu$_{100}$-Leu-Pro-Ala | 88 |

FIG. 4A

| MMP-2 | | |
|---|---|---|
| Guinea pig α1 (I)gelatin | Gly-Ala-Hyp-Gly$_{547}$~Leu$_{548}$-Glx-Gly-His | 24 |
| Rat α1 (I) gelatin | Gly-Pro-Gln-Gly$_{190}$~Val$_{191}$-Arg-Gly-Glu | 30 |
| Rat α1 (I) gelatin | Gly-Pro-Ala-Gly$_{277}$~Val$_{278}$-Gln-Gly-Pro | 30 |
| Rat α1 (I) gelatin | Gly-Pro-Ser-Gly$_{301}$~Leu$_{302}$-Hyp-Gly-Pro | 30 |
| Rat α1 (I) gelatin | Gly-Pro-Ala-Gly$_{331}$~Glu$_{332}$-Arg-Gly-Ser | 30 |
| Rat α1 (I) gelatin | Gly-Ala-Lys-Gly$_{361}$~Leu$_{362}$-Thr-Gly-Ser | 30 |
| Rat α1 (I) gelatin | Gly-Pro-Ala-Gly$_{382}$~Gln$_{383}$-Asp-Gly-Pro | 30 |
| Rat α1 (I) gelatin | Gly-Pro-Ala-Gly$_{634}$~Phe$_{635}$-Ala-Gly-Pro | 30 |
| Rat α1 (I) gelatin | Gly-Pro-Ile-Gly$_{676}$~Asn$_{677}$-Val-Gly-Ala | 30 |
| Rat α1 (I) gelatin | Gly-Pro-Hyl-Gly$_{685}$~Ser$_{686}$-Arg-Gly-Ala | 30 |
| Bovine type 1 collagen (α1) | Gly-Pro-Gln-Gly$_{775}$~Ile$_{776}$-Ala-Gly-Gln | 22 |
| Bovine type 1 collagen (α2) | Gly-Pro-Gln-Gly$_{775}$~Leu$_{776}$-Leu-Gly-Ala | 22 |
| Human aggrecan | Ile-Pro-Glu-Asn$_{341}$~Phe$_{342}$-Phe-Gly-Val | 89 |
| Human galectin-3 | Pro-Pro-Gly-Ala$_{62}$ ~Tyr$_{63}$ -His-Gly-Ala | 90 |
| Human cartilage link | Arg-Ala-Ile-His$_{16}$ ~Ile$_{17}$ -Gln-Ala-Glu | 87 |
| Human cartilage link | Gly-Pro-His-Leu$_{25}$ ~Leu$_{26}$ -Val-Glu-Ala | 87 |
| Human insulin-like growth factor binding protein-3 | Leu-Arg-Ala-Tyr$_{99}$ ~Leu$_{100}$-Leu-Pro-Ala | 88 |

FIG.4B

MMP-3

| Substrate | Sequence | % |
|---|---|---|
| Human α$_2$-macroglobulin | Gly-Pro-Glu-Gly$_{679}$~Leu$_{680}$-Arg-Val-Gly | 79 |
| Human α$_2$-macroglobulin | Arg-Val-Gly-Phe$_{684}$~Tyr$_{685}$-Glu-Ser-Asp | 79 |
| Human α$_1$-antichymotrypsin | Leu-Leu-Ser-Ala$_{360}$~Leu$_{361}$-Val-Glu-Thr | 91 |
| α$_1$-protease inhibitor | Glu-Ala-Ile-Pro$_{357}$~Met$_{358}$-Ser-Ile-Pro | 91 |
| Antithrombin III | Ile-Ala-Gly-Arg$_{385}$~Ser$_{386}$-Leu-Asn-Pro | 91 |
| Chicken ovostatin | Leu-Asn-Ala-Gly$_{677}$~Phe$_{678}$-Thr-Ala-Ser | 79, 92 |
| Human aggrecan | Ile-Pro-Glu-Asn$_{341}$~Phe$_{342}$-Phe-Gly-Val | 93 |
| Substance P | Lys-Pro-Gln-Gln$_6$~Phe$_7$ -Phe-Gly-Leu | 37 |
| Human ProMMP-1 | Asp-Val-Ala-Gln$_{80}$ ~Phe$_{81}$ -Val-Leu-Thr | 43 |
| Human ProMMP-3 | Asp-Thr-Leu-Glu$_{68}$ ~Val$_{69}$ -Met-Arg-Lys | 94 |
| Human ProMMP3 | Asp-Val-Gly-His$_{82}$ ~Phe$_{83}$ -Arg-Thr-Phe | 94 |
| Human ProMMP-8 | Asp-Ser-Gly-Gly$_{78}$ ~Phe$_{79}$ -Met-Leu-Thr | 95 |
| Human ProMMP-9 | Arg-Val-Ala-Glu$_{40}$ ~Met$_{41}$ -Arg-Gly-Glu | 48 |
| Human ProMMP-9 | Asp-Leu-Gly-Arg$_{87}$ ~Phe$_{88}$ -Gln-Thr-Phe | 48 |
| Human fibronectin | Pro-Phe-Ser-Pro$_{689}$~Leu$_{690}$-Val-Ala-Thr | 21 |
| Human insulin-like growth factor binding protein-3 | Leu-Arg-Ala-Tyr$_{99}$ ~Leu$_{100}$-Leu-Pro-Ala | 88 |
| | Ala-Pro-Gly-Asn$_{109}$~Ala$_{110}$-Ser-Glu-Ser | 88 |
| | Phe-Ser-Ser-Glu$_{176}$~Ser$_{177}$-Lys-Arg-Glu | 88 |
| Bovine α1(II)collagen,N-telopeptide | Ala-Gly-Gly-Ala$_{115}$~Gln$_{116}$-Met-Gly-Val | 96 |
| Bovine α1(II)collagen,N-telopeptide | Gln-Met-Gly-Val$_{119}$~Met$_{120}$-Gln-Gly-Pro | 96 |
| Bovine a1(IX)collagen,NC2 | Met-Ala-Ala-Ser ~Leu -Lys-Arg-Pro | 96 |
| Bovine a2(IX)collagen,NC2 | ~Ala -Lys-Arg-Glu | 96 |
| Bovine a3(IX)collagen,NC2 | ~Leu -Arg-Lys-Pro | 96 |
| Bovine α1(XI)collagen,N-telopeptide | Gln-Ala-Gln-Ala ~Ile -Leu-Gln-Gln | 96 |
| Human cartilage link | Arg-Ala-Ile-His$_{16}$ ~Ile$_{17}$ -Gln-Ala-Glu | 87 |
| Bovine insulin,B chain | Leu-Val-Glu-Ala$_{14}$ ~Leu$_{15}$ -Tyr-Leu-Val | 97 |
| Bovine insulin,B chain | Glu-Ala-Leu-Tyr$_{16}$ ~Leu$_{17}$ -Val-Cys-Gly | 21, 97 |

FIG. 4C

MMP-7
Human aggrecan                Ile-Pro-Glu-Asn$_{341}$~Phe$_{342}$-Phe-Gly-Val         89
Human cartilage link          Gly-Pro-His-Leu$_{25}$ ~Leu$_{26}$ -Val-Glu-Ala         87
Human prourokinase            Pro-Pro-Glu-Glu$_{143}$~Leu$_{144}$-Lys-Phe-Gln         98

MMP-9
Human type V collagen (α1)    Gly-Pro-Pro-Gly$_{439}$~Val$_{440}$-Val-Gly-Pro          99
Human type V collagen (α2)    Gly-Pro-Pro-Gly$_{445}$~Leu$_{446}$-Arg-Gly-Glu          99

Human type XI collagen (α1)   Gly-Pro-Gly-Gly$_{439}$~Val$_{440}$-Val-Gly-Pro          99
Human aggrecan                Ile-Pro-Glu-Asn$_{341}$~Phe$_{342}$-Phe-Gly-Val          89
Human galectin-3              Pro-Pro-Gly-Ala$_{62}$ ~Tyr$_{63}$ -His-Gly-Ala          90
Human cartilage link          Arg-Ala-Ile-His$_{16}$ ~Ile$_{17}$ -Gln-Ala-Glu          87

MMP-10
Human cartilage link          Arg-Ala-Ile-His$_{16}$ ~Ile$_{17}$ -Gln-Ala-Glu          87
Human cartilage link          Gly-Pro-His-Leu$_{25}$ ~Leu$_{26}$ -Val-Glu-Ala          87

FIG.4D

LATENT FUSION PROTEIN

The present invention relates to the use of DNA constructs, and proteins encoded by the constructs, in medicine with particular application in gene therapy. The present invention also relates to methods of providing latency to pharmaceutically active agents.

Most cytokines and growth factors are expressed under tight control mechanisms. Their gene expression is regulated by environmental stimuli such as infection, cell-cell interactions, cage in extracellular matrix composition and interactions with adhesion molecules or via stimulation with other cytokines.

In addition to the control at the transcriptional and post-transcriptional level, some cytokines are not released into the medium unless a second signal activates the cell. A third level of regulation for cytokine activity is found in molecules which are secreted in a latent form and become "activated" by releasing the cytokine moiety where processes of inflammation, wound healing and tissue repair takes place (Khalil N, Microbes and Infection, 1, 1255–1263 (1999). In this latter respect, transforming growth factor beta (TGFβ) has received greatest attention.

TGFβ is synthesized as a dimeric latent cytokine composed of an amino terminal latency associated protein (LAP) ad the active TGFβ cytokine at its COOH terminal end (Roberts and Sporn, Peptide Growth Factors and their Receptors: Sporn, M B and Roberts, A B, Springer-Verlag, 419–472 (1996); Roth-Eicchorn et al., Hepatology, 28 1588–1596 (1998)). The precursor peptide contains a signal peptide (residues 1–29) necessary for protein secretion and guiding the molecule through the Golgi apparatus to become processed by proteolytic cleavage and glycosylation. The LAP domain is separated from TGFβ by proteolytic cleavage at arginines (277–278). Mature TGFβ begins at alanine 279. The LAP, in addition to protect TGFβ, contains important residues necessary for the interaction with other molecules. Mutations in the LAP domain have recently been associated with the autosomal dominant Camurati-Engelmann disease (Janssens et al., Nature Genetics, 26, 273:275 (2000). Cysteines 224 and 226 are important in the intermolecular disulphide bond between two LAPs. Their mutation to serine renders the molecule "active" (Sanderson et al., Proc. Natl. Acad. Sci. USA, 92, 2572–2576 (1995); Brunner et al., Mol. Endocrinol. 6, 1691–1700 (1992); Brunner et al., J. Biol. Chem, 264, 13660–13664 (1989)). The RGD motif (245–247) facilitates the interaction with integrins (Munger et al., Mol, Biol. of the Cell, 9, 2627–2638 (1998; Derynck R, TIBS, 19, 548–553 (1994)). Nucleic acid encoding TGFβ is described in U.S. Pat. No. 5,801,231.

In most cell types studied, including those of mesenchymal, epithelial and endothelial origin, TGFβ is secreted in a latent form consisting of TGFβ and its latency associated peptide (LAP) propeptide dimers, covalently linked to latent TGFβ-binding proteins (LTBPs). LTBPs are also needed for the secretion and folding of TGFβ (Miyazano et al., EMBO J. 10, 1091–1101 (1991); Miyazano et al., J. Biol. Chem. 267, 5668–5675 (1992); Eklov et al., Cancer Res. 53, 3193–3197 (1993)). Cysteine 33 is important for the disulphide bridge with the third 8 cysteine-rich repeat of latent TGFβ binding protein (LTBP) (Saharinen et al., The EMBO Journal, 15, 245–253 (1996). Modification of LTBP by enzymes such as thrombospondin (Schultz et al., The Journal of Biological Chemistry, 269, 26783–26788 (1994); Crawford et al., Cell, 93, 1159–1170 (1998)), transglutaminase (Nunes et al., J. Cell, Biol. 136, 1151–1163 (1997); Kojima et al., The Journal of Cell Biology, 121, 439–448 (1993)) and MMP9, MMP2 (Yu and Stamenkovic, Genes and Dev, 14, 163–176 (2000)) could release the active portion of TGFβ from the latent complex.

Cytokines are natural products serving as soluble local mediators of cell-cell interactions. They have a variety of pleiotropic actions, some of which can be harnessed for therapeutic purposes. Targeting of cytokines to specific cell types using scFv (Lode et al., Pharmacol. Ther, 80, 277–292 (1998)) and vWF (Gordon et al., Human Gene Therapy, 8, 1385–1394 (1997)) have focused entirely on the active cytokine moiety of the cytokine complex.

Pharmacologically active proteins or other medicines based on such agents, which have to be administered at very high concentrations systemically in order to achieve biologically effective concentrations in the tissue being targeted, tend to give rise to undesirable systemic effects, for example toxicity, which limit their use and efficacy.

The present inventors have developed a system for overcoming the toxic effect of systemic administration of potent biological agents.

According to a first aspect of the invention there is provided the use of a fusion protein comprising a latency associated peptide (LAP) and a proteolytic cleavage site for providing latency to a pharmaceutically active agent.

According to a second aspect of the invention there is provided a method of providing latency to a pharmaceutically active agent comprising associating a fusion protein comprising a latency associated peptide (LAP) and a proteolytic cleavage site with said pharmaceutically active agent.

The term "protein" in this text means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues and derivatives of a protein wherein the fragment, analogue or derivative retains essentially the same biological activity or function as a reference protein.

The fragment, derivative or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half life of the polypeptide (for example, polyethylene glycol), or (iv) one in which the additional amino acids are fused to the mature polypeptide, such as a leader or secretory sequence which is employed for purification of the polypeptide. Such fragments, derivatives and analogues are deemed to be within the scope of those skilled in the art from the teachings herein.

Particularly preferred are variants, analogues, derivatives and fragments having the amino acid sequence of the protein in which several e.g. 5 to 10, 1 to 5, 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions.

An example of a variant of the present invention is a fusion protein as defined above, apart from the substitution of one or more amino acids with one or more other amino acids. The skilled person is aware that various amino acids have similar properties. One or more such amino acids of a substance can often be substituted by one or more other such amino acids without eliminating a desired, activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence given in a) above can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

The term "fusion protein" in this text means, in general terms, one or more proteins joined together by chemical means, or by peptide bonds through protein synthesis or both.

The latency associated peptide (LAP) of the present invention may include, but is not limited to, the coding sequence for the precursor domain of TGFβ or a sequence which is substantially identical thereto.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. 215, 403 (1990)).

The LAP of the present invention may comprise the precursor domain of TGFβ, for example, the precursor peptide of TGFβ-1, 2 or 3 (from human) (Derynck et al., Nature, 316, 701–705 (1985); De Martin et al., EMBO J. 6 3673–3677 (1987); Hanks et al., Proc. Natl. Acad. Sci. 85, 79–82 (1988); Derynck et al., EMBO J. 7, 3737–3743 (1988); Ten Dyke et al., Proc. Natl. Acad. Sci. USA, 85, 4715–4719 (1988)) TGFβ-4 (from chicken) (Jakowlew et al., Mol. Endocrinol. 2, 1186–1195 (1988)) or TGFβ-5 (from xenopus) (Kondaiah et al., J. Biol. Chem. 265, 1089–1093 (1990)). The term "precursor domain" is defined as a sequence encoding a precursor peptide which does not include the sequence encoding the mature protein. The amino acid sequences of the precursor domain of TGFβ 1, 2, 3, 4 and 5 (Roberts and Sporn, Peptide Growth Factors and their Receptors: Sporn, M B and Roberts, A B, Springer-Verlag, Chapter 8, 422 (1996)) are shown in FIG. 3.

Preferably, the amino acid sequence of the LAP has at least 50% identity, using the default parameters of the BLAST computer program (Atschul et al., J. Mol. Biol. 215, 403–410 (1990) provided by HGMP (Human Genome Mapping Project), at the amino acid level, to the precursor domain of TGFβ 1, 2, 3, 4 or 5 (Roberts and Sporn, Peptide Growth Factors and their Receptors: Sporn, M B and Roberts, A B, Springer-Verlag, Chapter 8, 422 (1996)) as shown in FIG. 3. More preferably, the LAP may have at least 60%, 70%, 80%, 90% and still more preferably 95% (still more preferably at least 99%) identity, at the nucleic acid or amino acid level, to the precursor domain of TGFβ 1, 2, 3, 4 or 5 as shown in FIG. 3.

The LAP may comprise the LAP of TGFβ 1, 2, 3, 4, or 5 (Roberts and Sporn, Peptide Growth Factors and their Receptors: Sporn, M B and Roberts, A B, Springer-Verlag, Chapter 8, 422 (1996)) as shown in FIG. 3.

The LAP may contain at least two, for example at least 4, 6, 8, 10 or 20 cysteine residues for the formation of disulphide bonds.

The LAP may provide a protective "shell" around the pharmaceutically active agent thereby shielding it and hindering, or preventing, its interaction with other molecules in the cell surface or molecules important for its activity.

The LAP may comprise the sequence of amino acids encoded by nucleotides 1–832 of FIG. 1 or nucleotides 598–1352 of FIG. 2 or a sequence which has at least 50%, 60%, 70%, 80%, 90%, 95% or 99% identity, using the default parameters of the BLAST computer program provided by HGMP, thereto.

The proteolytic cleavage site may comprise any protease specific cleavage site. The proteolytic cleavage site may include, but is not limited to, a matrix metalloproteinase (MMP) cleavage site, a serine protease cleavage site, a site cleavable by a parasitic protease derived from a pathogenic organism (Zhang et al., J. Mol. Biol. 289, 1239–1251 (1999); Voth et al., Molecular and Biochemical Parasitology, 93, 31–41 (1998); Yoshioka et al., Folia Pharmacologica Japonica, 110, 347–355 (1997); Tort et al., Advances in Parasitology, 43, 161–266 (1999); McKerrow, International Journal for Parasitology, 29, 833–837 (1999); Young et al., International Journal for Parasitology, 29, 861–867 (1999);

Coombs and Mottram, Parasitology, 114, 61–80 (1997)) or a site cleavable by the proteins of the complement cascade (Carroll, Annu. Rev. Immunol. 16, 545–568 (1998); Williams et al., Ann. Allergy, 60, 293–300 (1988)).

The MMP cleavage site may comprise any amino acid sequence which is cleavable by a MMP. The amino acid sequence of the MMP cleavage site may be encoded by nucleotides 844–861 of FIG. 1 or nucleotides 565–585 of FIG. 2 or a sequence of nucleotides which has at least 50%, 60%, 70%, 80%, 90%, 95% or 99% identity, using the default parameters of the BLAST computer program provided by HGMP, thereto. Preferably, the nucleic acid sequence encoding the MMP cleavage site comprises the minimum number of residues required for recognition and cleavage by MMP.

A MMP cleavage site may comprise a number of amino acid residues recognisable by MMP. Moreover, the amino acids of the MMP site may be linked by one or more peptide bonds which are cleavable, proteolytically, by MMP. MMPs which may cleave the MMP site include, but are not limited to, MMP1, MMP2, MMP3, MMP7, MMP8, MMP9 or MMP10 (Yu and Stamenkovic, Genes and Dev. 14, 163–176 (2000); Nagase and Fields, Biopolymers, 40, 399–416 (1996); Massova et al., J. Mol. Model. 3, 17–30 (1997); reviewed in Vu and Werb, Genes and Dev. 14, 2123–2133 (2000)). The sequences of the protein cleavage sites of MMP1, MMP2, MMP3, MMP7, MMP8, MMP9 and MMP10 are shown in FIG. 4.

Preferably, the proteolytic cleavage site of the present invention is cleaved at sites of inflammation and tissue remodelling. More preferably, the proteolytic cleavage site of the present invention is a MMP cleavage site e.g any one or more of MMP1, MMP2, MMP3, MMP7, MMP8, MMP9 or MMP10 as shown in FIG. 4.

The invention further provides nucleic acid encoding the fusion protein of the first and second aspects of the invention. The nucleic acid ending the fusion protein may comprise nucleotides 1–861 of FIG. 1 or nucleotides 585–1352 of FIG. 2 or a sequence of nucleotides which has at least 50%, 60%, 70%, 80%, 90%, 95% or 99% identity, using the default parameters of the BLAST computer program provided by HGMP, thereto.

The present invention may further provide a "linker" peptide. Preferably the linker peptide is linked to the amino acid sequence of the proteolytic cleavage site. The linker peptide may be provided at the C terminal or N terminal end of the amino acid sequence encoding the proteolytic cleavage site. Preferably, the linker peptide is continuous with the amino acid sequence of the proteolytic cleavage site. The linker peptide may comprise the amino acid sequence encoded by nucleotides 831–843 and/or 862–873 of FIG. 1 or nucleotides 553–564 and/or 586–597 of FIG. 2 or a sequence of nucleotides which has at least 50%, 60%, 70%, 80%, 90%, 95% or 99% identity, using the default parameters of the BLAST computer program provided by HGMP, thereto.

The term "linker peptide" is intended to define any sequence of amino acid residues which preferably provide a hydrophilic region when contained in an expressed protein. Such a hydrophilic region may facilitate cleavage by an enzyme at the proteolytic cleavage site.

The term "latency" as used herein, may relate to a shielding effect which may hinder interaction between the fusion protein and other molecules in the cell surface. Alternatively the term latency may be used to describe a reduction in the activity (up to and including ablation of activity) of a molecule/agent associated with the fusion protein. The term latency may also relate to a stabilising effect of the fusion protein. The effect may be in full or partial, where a partial effect is sufficient to achieve the latency of the active agent.

The pharmaceutically active agent may include, but is not limited to, a growth factor (eg. TGFβ, epidermal growth factor (EGF), platelet derived growth factor (PDGF), nerve growth factor (NGF), colony stimulating factor (CSF), hepatocyte growth factor, insulin-like growth factor, placenta growth factor); differentiation factor; cytokine eg. interleukin, (eg. IL1, IL-2, IL-3, IL-4, IL-5, IL-6, IL7, IL-8, IL-9, IL-10, IL-11, IL-12, IL-13, IL-14, IL-15, IL-16, IL-17, IL-18, IL-19, IL-20 or IL-21, either α or β), interferon (eg. IFN-α, IFN-β and IFN-γ), tumour necrosis factor (TNF), IFN-γ inducing factor (IGIF), bone morphogenetic protein (BMP); chemokine (eg. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); trophic factors; cytokine inhibitors; cytokine receptors; free-radical scavenging enzymes e.g. superoxide dismutase or catalase; peptide mimetics; protease inhibitors; tissue inhibitor of metalloproteinase sub classes (TIMPS) and serpins (inhibitors of serine proteases). Preferably, the pharmaceutically active agent will be derived from the species to be treated e.g., human origin for the treatment of humans. Preferably, the pharmaceutically active agent is IFNβ.

The pharmaceutically active agent may comprise a chemical compound such as a chemotherapeutic agent or other synthetic drug. Alternatively, the pharmaceutically active agent may comprise a peptide nucleic acid (PNA) sequence e.g a poly-lysine sequence which binds to nucleic acids and permeabilises lipid bilayers (Wyman et al., Biological Chemistry, 379, 1045–1052 (1998)) or a KALA peptide which facilitates transfer through lipid bilayers Wyman et al., Biochemisty, 36, 3008–3017 (1997)).

The term "associating with" in the context of the present invention is intended to include all means of association including, but not limited to, chemical cross-linking or peptide bond linkage.

In an alternative embodiment, the invention further provides the fusion protein of the present invention optionally in association with latent TGFβ binding protein (LTBP). Typically, the fusion protein is covalently linked to LTPB to form a complex. Preferably, the association is mediated by disulphide bond(s) between Cys No. 33 of LAP and the third 8 Cys residue of LTBP. The LTBP associated with the fusion protein may include, but is not limited to, LTBP 1, 2, 3 or 4 (Kanzaki et al., Cell, 61, 1051–1061 (1990); Tsuji et al., Proc. Natl. Acad. Sci. USA, 87, 8835–8839 (1990); Moren et al., J. Biol. Chem. 269, 32469–32478 (1994); Yin et al., J. Biol. Chem. 270, 10147–10160 (1995); Gibson et al., Mol. Cell. Biol. 15, 6932–6942 (1995); Saharinen et al., J. Biol. Chem. 273, 18459–18469 (1998)), or fragments of LTBP such as that containing the third 8 Cys repeat, or homologues having a sequence of amino acids or nucleotides which has at least 50%, 60%, 70%, 80%, 90%, 95% or 99% identity, using the default parameters of the BLAST computer program provided by HGMP, to that of LTBP. Cleavage of LTBP may release the fusion protein from the LTBP complex. Enzymes which may cleave LTBP in this manner include, but are not limited to, thrombospondin (Schultz et al., The Journal of Biological Chemistry, 269, 26783–26788 (1994); Crawford et al., Cell, 93, 1159–1170 (1998)), transglutaminase (Nunes et al., J. Cell, Biol. 136, 1151–1163 (1997); Kojima et al., The Journal of Cell Biology, 121, 439–448 (1993)) MMP9 and MMP2 (Yu and Stamenkovic, Genes and Dev, 14, 163–176 (2000)).

A third aspect of the invention provides a nucleic acid construct comprising a first nucleic acid sequence encoding a pharmaceutically active agent, a second nucleic acid sequence encoding a LAP, wherein a nucleic acid sequence encoding a proteolytic cleavage site is provided between the first and second nucleic acid sequences.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

Preferably, the first nucleic acid sequence encodes the protein IFNβ. The first nucleic acid sequence may comprise the sequence of nucleotides from 874–1376 of FIG. 1 or nucleotides 598–1352 of FIG. 2, or a sequence which is substantially homologous thereto. In one embodiment of the invention, the first nucleic acid sequence encodes IFNβ from a mouse or a human.

The nucleic acid construct of the third aspect of the invention may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

Preferably, the nucleic acid construct is LAP-mIFNβ as shown in FIG. 1 and schematically in FIG. 5 or mIFNβ-LAP as shown in FIG. 2 and schematically in FIG. 5.

The invention further provides a protein encoded by the nucleic acid construct of the third aspect of the invention optionally in association with latent TGFβ binding protein (LTBP) described herein. Typically, the protein encoded by tar nucleic acid construct is covalently linked to LTBP to form a complex. Preferably, the association is mediated by disulphide bond(s) between Cys No. 33 of LAP and the third 8 Cys residue of LTBP.

The nucleic acid construct of the third aspect of the invention preferably includes a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidinekinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA elements without enhancer elements) for example, the minimum sequence of the CMV promoter.

Preferably, the promoter is contiguous to the first and/or second nucleic acid sequence.

As stated herein, the nucleic acid construct of the third aspect of the invention may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

One embodiment of the invention relates to a cell comprising the nucleic acid construct of the third aspect of the invention. The cell may be termed a "host" cell, which is useful for the manipulation of the nucleic acid, including cloning. Alternatively, the cell may be a cell in which to obtain expression of the nucleic acid. Representative examples of appropriate host cells for expression of the nucleic acid construct of the invention include virus packaging cells which allow encapsulation of the nucleic acid into a viral vector; bacterial cells, such as *streprococci, staphylococci, E. coli, streptomyces* and *Bacillus Subtilis*; single cells, such as yeast cells, for example, *Saccharomyces Cerevisiae*, and *Aspergillus* cells; insect cells such as *Drosophila* S2 and *Spodoptra* Sf9 cells, and cells such as CHO, COS, C127, 3T3, PHK.293, and Bowes Melanoma cells and other suitable human cells; and plant cells e.g. *Arabidopsis thaliana*.

Induction of an expression vector into the host cell can be affected by calcium phosphate transfection, DEAE-dextran mediated transfection, microinjection, cationic—lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Coldspring Harbor Laboratory Press, Coldspring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryocic and eukaryotic host are described by Sambrook et al, Molecular Cloning, a Laboratory Manual, Second Edition, Coldspring Harbor Laboratory Press, Coldspring Harbor, N.Y. (1989).

Proteins can be recovered and purified from recombinant cell cultures by well-known methods including ammonium sulphate or ethanol precipitation, acid extraction, anion or cation exchange chromatography, phoshocellulose chromatography, hydrophobic interaction chromatography, affinity chromatography, hydroxylapatite chromatography, high performance liquid chromatography and lectin chromatography. For therapy, the nucleic acid construct e.g. in the form of a recombinant vector, may be purified by techniques known in the art, such as by means of column chromatography as described in Sambrook et al, Molecular Cloning, a Laboratory Manual, Second Edition, Coldspring Harbor Laboratory Press, Coldspring Harbor, N.Y. (1989).

In a fourth aspect, the invention provides a method of treatment of a patient such as a mammal, including human, comprising administering to a recipient a therapeutically effective amount of the nucleic acid construct of the third aspect of the invention. Where the nucleic acid construct is used in the therapeutic method of the invention, the construct may be used as part of an expression construct, e.g in the form of an expression vector such as a plasmid or virus. In such a method, the construct may be administered intravenously, intradermally, intramuscularly, orally or by other routes.

The nucleic acid construct of the third aspect of the invention, and proteins derived therefrom, may be employed alone or in conjunction with other compounds, such as therapeutic compounds, e.g anti-inflammatory drugs, cytotoxic agents, cytostatic agents or antibiotics. The nucleic acid constructs and proteins useful in the present invention are preferably provided in an isolated form, and preferably are purified to homogeneity.

As used herein, the term "treatment" includes any regime that can benefit a human or a non-human animal. The treatment may be in respect of any existing condition or disorder, or may be prophylactic (preventive treatment). The treatment may be of an inherited or an acquired disease. The treatment may be of an acute or chronic condition. Preferably, the treatment is of a condition/disorder associated with inflammation. The first nucleic acid sequence of the nucleic acid construct of the third aspect of the invention may encode a protein for use in the treatment of the disorder, including, but not limited to osteoarthritis, scleroderma, renal disease, rheumatoid arthritis, inflammatory bowel disease, multiple sclerosis, atherosclerosis, cancer, or any inflammatory disease.

The nucleic acid construct of the third aspect of the invention may be used therapeutically in the method of the invention by way of gene therapy. Alternatively, protein encoded by the nucleic acid construct may be directly administered as described herein.

Administration of the nucleic acid construct of the third aspect may be directed to the target site by physical methods. Examples of these include topical administration of the "naked" nucleic acid in the form of a vector in an appropriate vehicle, for example, in solution in a pharmaceutically acceptable excipient, such as phosphate buffered saline, or administration of a vector by physical method such as particle bombardment according to methods known in the art.

Other physical methods for administering the nucleic acid construct or proteins of the third aspect of the invention directly to the recipient include ultrasound, electrical stimulation, electroporation and microseeding. Further methods of administration include oral administration or administration through inhalation.

Particularly preferred is the microseeding mode of delivery which is a system for delivering genetic material into cells in situ in a patient. This method is described in U.S. Pat. No. 5,697,901.

The nucleic acid construct according to the third aspect of the invention may also be administered by means of delivery vectors. These include viral delivery vectors, such as adenovirus or retrovirus delivery vectors known in the art.

Other non-viral delivery vectors include lipid delivery vectors, including liposome delivery vectors known in the art.

Administration may also take place via transformed host cells. Such cells include cells harvested from the subject, into which the nucleic acid construct is transferred by gene transfer methods known in the art. Followed by the growth of the transformed cells in culture and grafting to the subject.

As used herein the term "gene therapy" refers to the introduction of genes by recombinant genetic engineering of body cells (somatic gene therapy) or of cells of the germ line (germ-line therapy) for the benefit of the patient. Furthermore, gene therapy can be divided into ex vivo and in vivo techniques. Ex vivo gene therapy relates to the removal of body cells from a patient, treatment of the removed cells with a vector ie, a recombinant vector, and subsequent return of the treated cells to the patient. In vivo gene therapy relates to the direct administration of the recombinant gene vector by, for example, intravenous or intravascular means.

Preferably the method of gene therapy of the present invention is carried out ex vivo.

Preferably in gene therapy, the expression vector of the present invention is administered such that it is expressed in the subject to be treated. Thus for human gene therapy, the promoter is preferably a human promoter from a human gene, or from a gene which is typically expressed in humans, such as the promoter from human CMV.

For gene therapy, the present invention may provide a method for manipulating the somatic cells of human and non-human mammals.

The present invention also provides a gene therapy method which may involve the manipulation of the germ line cells of a non-human mammal.

The present invention therefore provides a method for providing a human with a therapeutic protein comprising introducing mammalian cells into a human, the human cells having been treated in vitro to insert therein a nucleic acid construct according to the third aspect of the invention.

Each of the individual steps of the ex vivo somatic gene therapy method are also covered by the present invention. For example, the step of manipulating the cells removed from a patient with the nucleic acid construct of the third aspect of the invention in an appropriate vector. As used herein, the term "manipulated cells" covers cells transfected with a recombinant vector.

Also contemplated is the use of the transfected cells in the manufacture of a medicament for the treatment of an inflammatory disorder.

A fifth aspect of the invention provides a nucleic acid construct, or protein encoded thereby, according to the third aspect of the invention for use in medicine, preferably for use in gene therapy.

A sixth aspect of the invention provides for the use of the nucleic acid construct according to the third aspect of the invention in the manufacture of a medicament for the treatment of an inflammatory disorder. In this context, the inflammatory disorder may include any one or more of the inflammation associated conditions discussed above.

The present invention also relates to compositions comprising the nucleic acid construct or proteins of the third aspect of the invention. Therefore, the nucleic acid construct of the present invention may be employed in combination with the pharmaceutically acceptable carrier or carriers. Such carriers may include, but are not limited to, saline, buffered saline, dextrose, liposomes, water, glycerol, ethanol and combinations thereof.

The pharmaceutical compositions may be administered in any effective, convenient manner effective for treating a patients disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg. The physician in any event will determine the actual dosage which will be most suitable for an individual which will be dependant on factors including the age, weight, sex and response of the individual. The above dosages are exemplary of the average case. There can, of course, be instances where higher or lower dosages are merited, and such are within the scope of this invention.

A seventh aspect of the invention provides a fusion protein comprising a LAP and a proteolytic cleavage site wherein the fusion protein is associated with a pharmaceutically active agent.

The invention further provides a nucleic acid construct encoding the fusion protein of the seventh aspect of the invention. The nucleic acid construct preferably comprises a nucleic acid sequence encoding a LAP adjacent a nucleic acid sequence encoding a proteolytic cleavage site. Preferably, the nucleic acid sequence encoding a LAP is suitably operably linked to a nucleic acid sequence encoding a proteolytic cleavage site. The nucleic acid construct encoding the fusion protein may comprise nucleotides 1–861 of FIG. 1 or nucleotides 585–1352 of FIG. 2 or a sequence of nucleotides which has at least 50%, 60%, 70%, 80%, 90%, 95% or 99% identity, using the default parameters of the BLAST computer program provided by HGMP, thereto.

The invention further provides the fusion protein of the seventh aspect of the invention optionally in association with latent TGFβ binding protein (LTBP) described herein.

The fusion protein of the seventh aspect of the invention may be associated with the pharmaceutically active agent by means of a peptide bond linkage. Alternatively, the fusion protein may be associated with the pharmaceutically active agent by means of a chemical linkage e.g. by cross-linking the fusion protein to a chemical compound such as a chemotherapeutic agent, synthetic drug or PNA.

Preferably, the pharmaceutically active agent is linked to the C-terminal end of the amino acid sequence of the proteolytic cleavage site in the fusion protein of the seventh aspect of the invention. More preferably, the pharmaceutically active agent is continuous with the C-terminal residue of the amino acid sequence of the proteolytic cleavage site.

An eighth aspect of the invention provides a process for preparing the fusion protein, and associated pharmaceutically active agent, of the seventh aspect of the invention comprising production of the fusion protein recombinantly by expression in a host cell, purification of the expressed fusion protein and association of the pharmaceutically active agent to the purified fusion protein by means of peptide bond linkage or chemical cross linking.

In a ninth aspect, the invention provides a method of treatment of a patient such as a mammal, including human, comprising administering to a recipient a therapeutically effective amount of the fusion protein, and associated pharmaceutically active agent, of the seventh aspect of the invention. In such a method, the fusion protein and associated pharmaceutically active agent may be administered intravenously, intradermally, intramuscularly, orally or by other routes.

The fusion protein, and associated pharmaceutically active agent of the seventh aspect of the invention may be employed alone or in conjunction with other compounds, such as therapeutic compounds, e.g anti-inflammatory drugs, cytotoxic agents, cyostatic agents or antibiotics.

Preferably, the fusion protein and associated pharmaceutically active agent of the seventh aspect of the invention are directly administered to a patient as described herein.

A tenth aspect of the invention provides a fusion protein and associated pharmaceutically active agent according to the seventh aspect of the invention for use in medicine.

An eleventh aspect of the invention provides for the use of the fusion protein and associated pharmaceutically active agent according to the seventh aspect of the invention in the manufacture of a medicament for the treatment of an inflammatory disorder. In this context, the inflammatory disorder may include any one or more of the inflammation associated conditions discussed herein.

The present invention also relates to compositions comprising the fusion protein and associated pharmaceutically active agent of the seventh aspect of the invention. Therefore, the fusion protein and associated pharmaceutically active agent may be employed in combination with the pharmaceutically acceptable carrier or carriers. Such carriers may include, but are not limited to, saline, buffered saline, dextrose, liposomes, water, glycerol, polyethylene glycol, ethanol and combinations thereof.

The pharmaceutical compositions may be administered in any effective, convenient manner effective for treating a patients disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

The invention also provides a kit of parts comprising a nucleic acid construct of the third aspect of the invention, or a fusion protein and associated pharmaceutically active agent according to the seventh aspect of the invention, and an adminstration vehicle including, but not limited to, tablets for oral administration, inhalers for lung administration and injectable solutions for intravenous administration.

All preferred features of the second and subsequent aspects of the invention are as for the first aspect mutatis mutandis.

The present invention will now be described by way of example only with reference to the accompanying figures wherein:

FIGS. 1A and 1B show nucleotide and corresponding amino acid sequence of the LAP-mIFNβ construct. The boxed sequence corresponds to the sequence of the MMP cleavage site including linker sequence;

FIGS. 2A and 2B show nucleotide and corresponding amino acid sequence of the mIFNβ-LAP construct. The boxed sequence corresponds to the sequence of the MMP cleavage site including linker sequence;

Figure 5A:
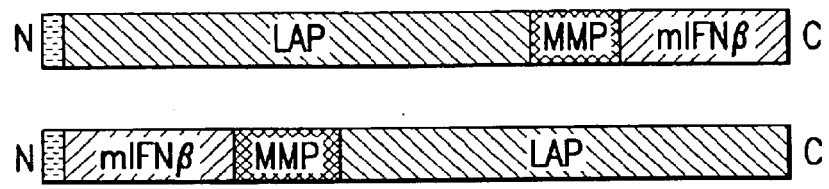
Figure 5B:
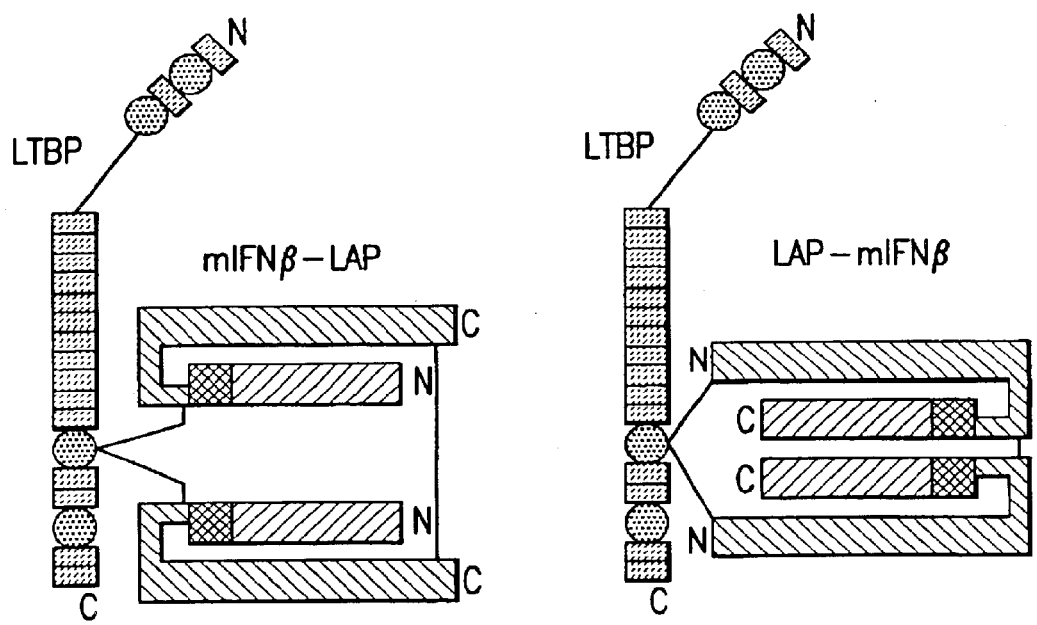
Figure 6:
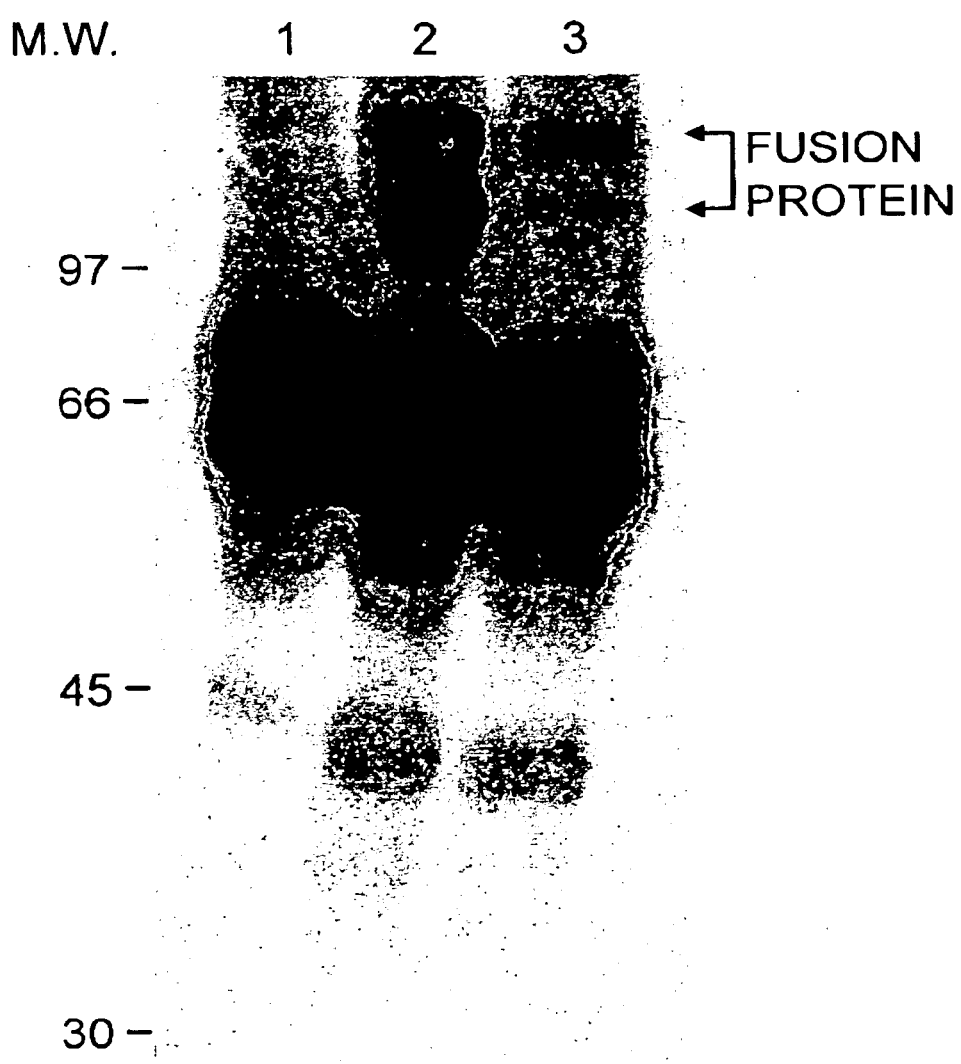
Figure 7:
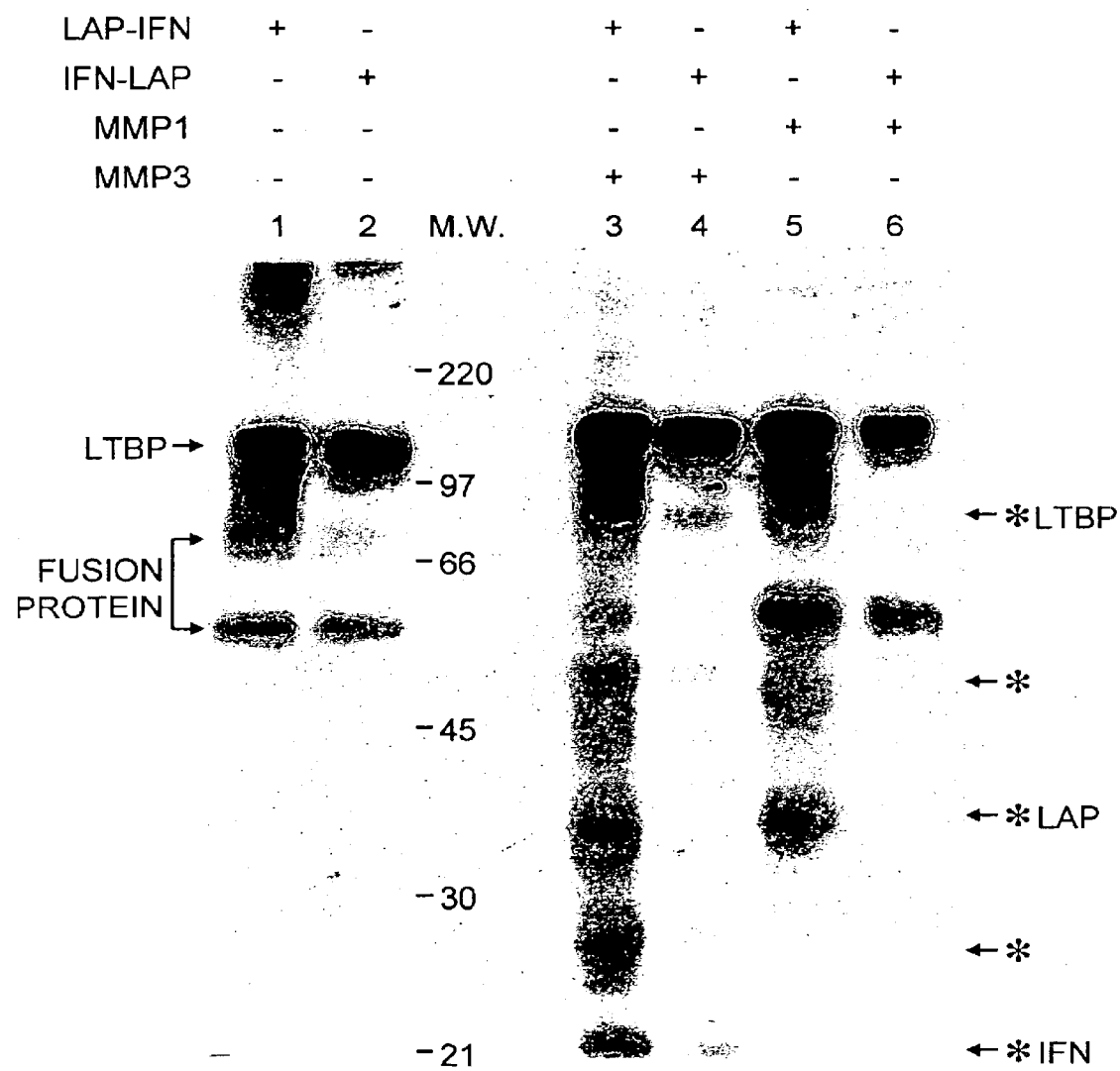
Figure 8A:
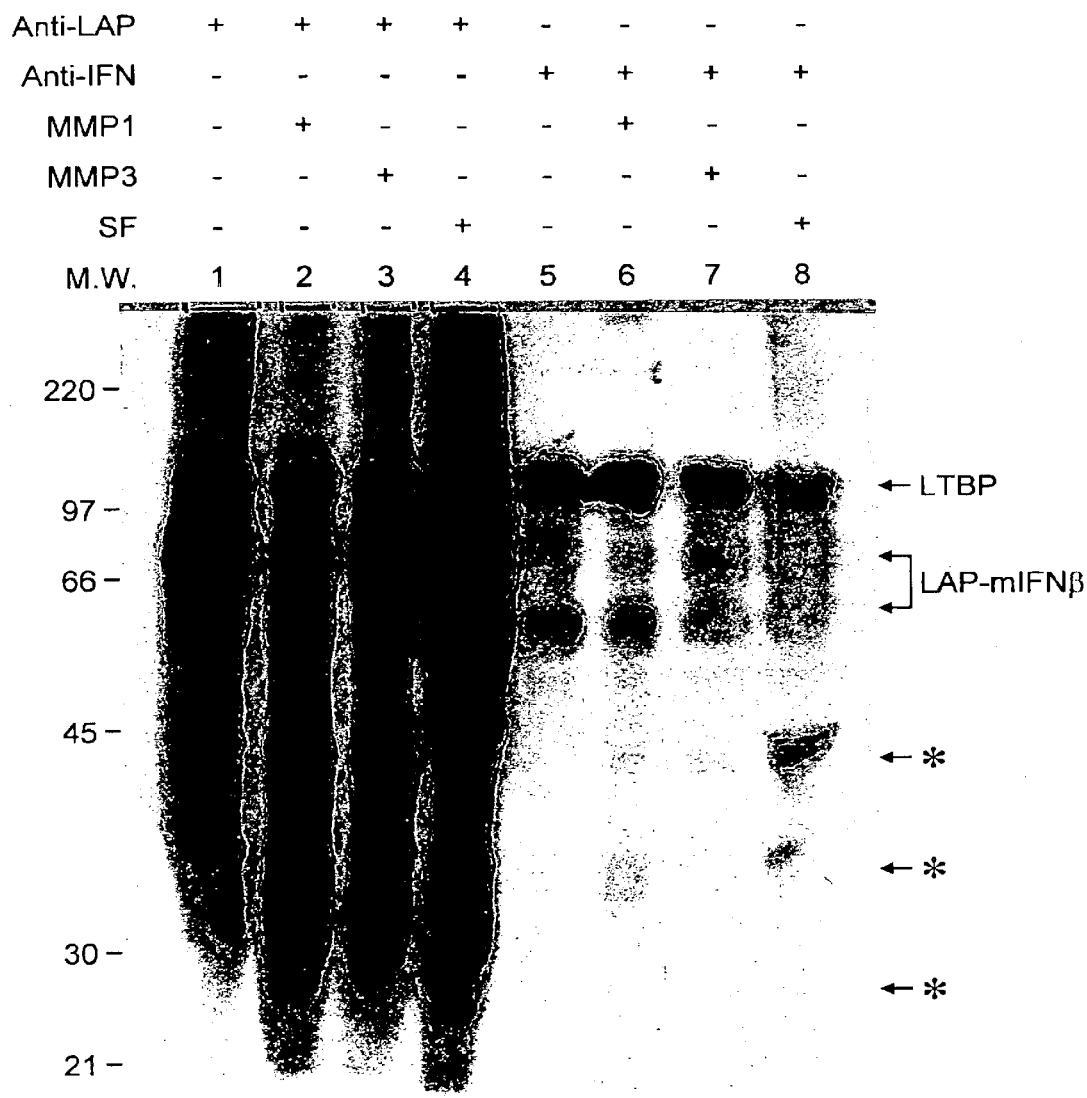
Figure 8B:
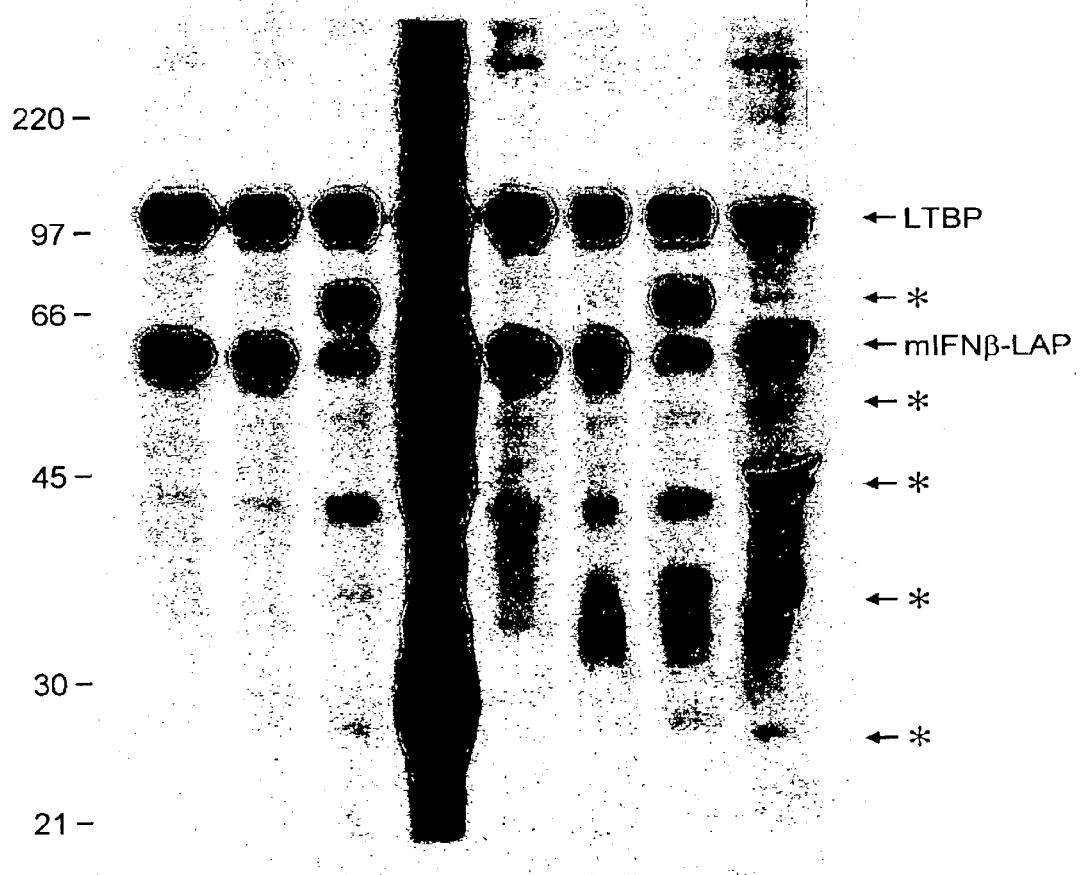
Figure 9A:
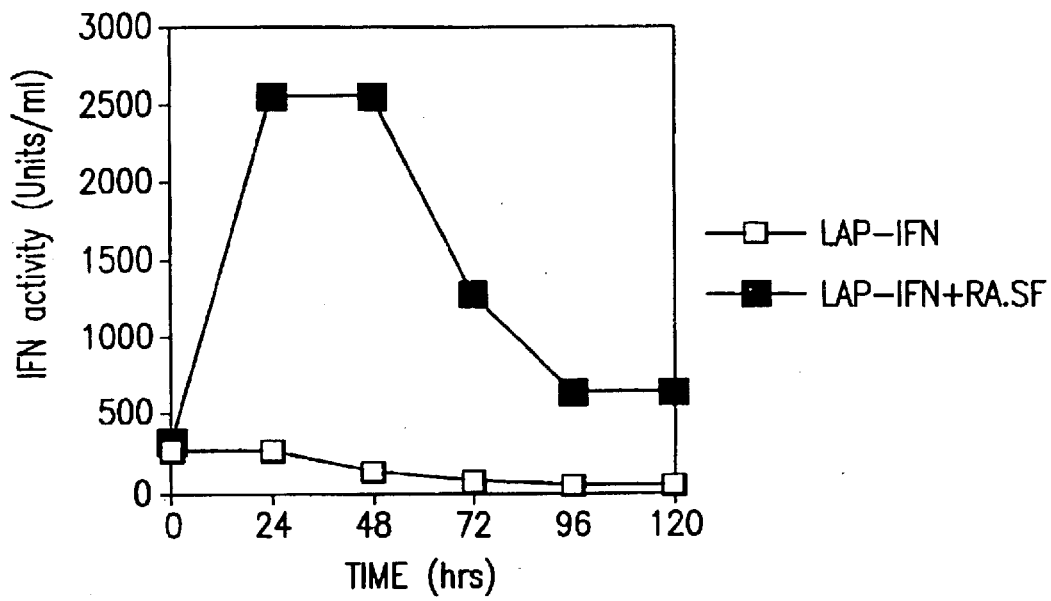
Figure 9B:
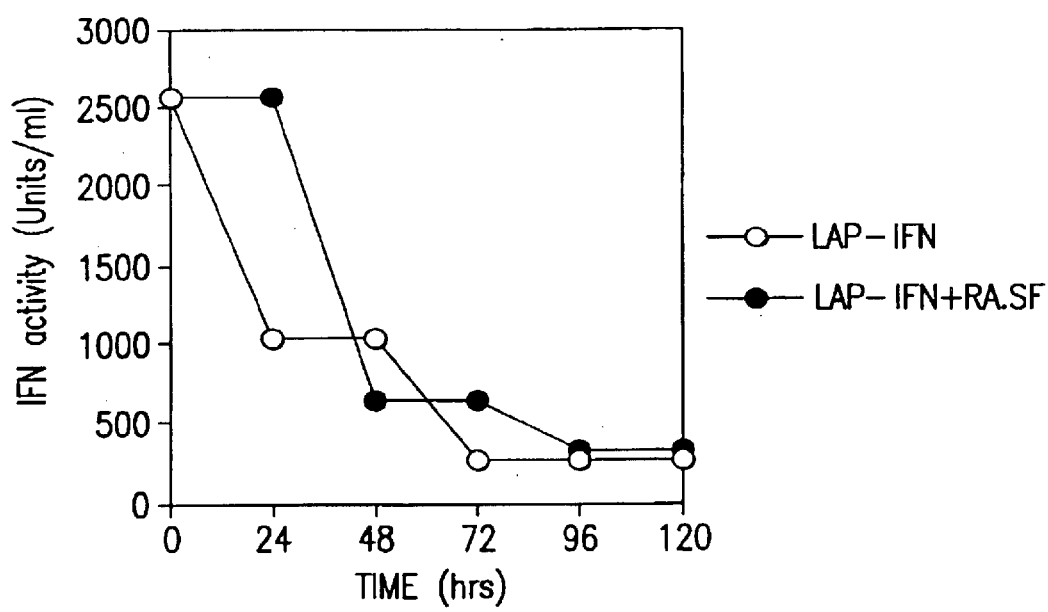

FIGS. 3A and 3B show amino acid sequences of the precursor domain of TGFβ1, 2, and 3 (human, Hu), TGFβ 4 (chicken, Ck), TGFβ (frog, Fg). Arrows indicate the position of the proteolytic processing resulting in cleavage of the signal peptide of TGFβ1 and of the mature TGFβs. N-linked glycosylation sites are underlined, as is the integrin cellular recognition sequence (Roberts and Sporn, Peptide Growth Factors and their Receptors: Sporn, MB and Roberts, AB, Springer-Verlag, Chapter 8, 422 (1996));

FIGS. 4A–4D show the sequences of protein cleavage sites of matrix metalloproteinases (MMPs) (Nagase and Fields, Biopolymers, 40, 399–416 (1996));

FIGS. 5A and 5B show schematic representation of the fusion proteins used in this study and their putative folding. (A) Primary structure of recombinant latent protiens. The linear sequence arrangement of the LAP, MMP and mIFNβ constituents in the two configurations used in this study, LAP-mIFNβ and mIFNβ-LAP, is shown. The box at the amino terminal end of LAP-mIFNβ and mIFNβ-LAP depicts the native signal sequence peptide for secretion of either TGFβ or mIFNβ respectively. (B) Putative folding and interactions with LTBP of latent cytokine. In LTBP, the EGF like repeats are shown as small squares, the cysteine-rich repeats and hybrid domain as circles, and the 'hinge region' which is sensitive to proteolytic cleavage is shown as a solid black line. Disulphide bonds are shown as solid grey lines; nucleotide (A) and corresponding amino acid (B) sequence of the LAP-mIFNβ construct. The boxed sequence corresponds to the sequence of the MMP cleavage site including linker sequence;

FIG. 6 shows detection of recombinant fusion proteins in supernatants of CHO cells. Non denaturing SDS-PAGE of supernatants from CHO cells (lane 1), LAP-mIFNβ transfected (lane 2) and mIFNβ-LAP (lane 3). Position of the double bands of newly expressed fusion proteins are marked by a double arrow. Position of the molecular weight markers (M.W.) in kDa is shown;

FIG. 7 shows immunoprecipitation of CHO cell supernatants with anti-LAP antibody and cleavage with MMP1 and MMP3. LAP-mIFNβ (lanes 1, 3 and 5) and mIFNβ-LAP (lanes 2, 4 and 6). Untreated controls (lanes 1 and 2), treated with MMP3 (lanes 3 and 4), treated with MMP1 (lanes 5 and 6). SDS PAGE was performed under denaturing conditions. The positions of LTBP and fusion proteins, are indicated by arrows. The arrows marked with an asterisk (*) indicates the presence of MMP cleavage products. Position of the molecular weight markers (M.W.) in kDa is shown;

FIGS. 8A–8B show immunoprecipitation of MTX-selected CHO cell supernatants with anti-LAP and anti-IFNβ antibodies and cleavage with MMP1, MMP3 and synovial fluid from rheumatoid arthrotis patients. (A). LAP-mIFNβ and (B). mIFNβ-LAP. Untreated supernatants (lanes 1 and 5), MMP1 treated (lanes 2 an 6), MMP3 treated (lanes 3 and 7) and rheumatoid arthritis synovial fluid treated (lanes 4 and 8). Immunoprecipitated with anti-LAP (lanes 1–4) and anti-IFNβ monoclonal antibody (lanes 5–8). The positions of LTBP and fusion proteins are indicated by arrows. The arrows marked with an asterisk (*) indicate the presence of MMP cleavage products;

FIGS. 9A and 9B show kinetics of IFN activity following incubation in medium alone or with rheumatoid arthritis synovial fluid. (A). LAP-mIFNβ; (B). mIFNβ-LAP.

Figure 10A:
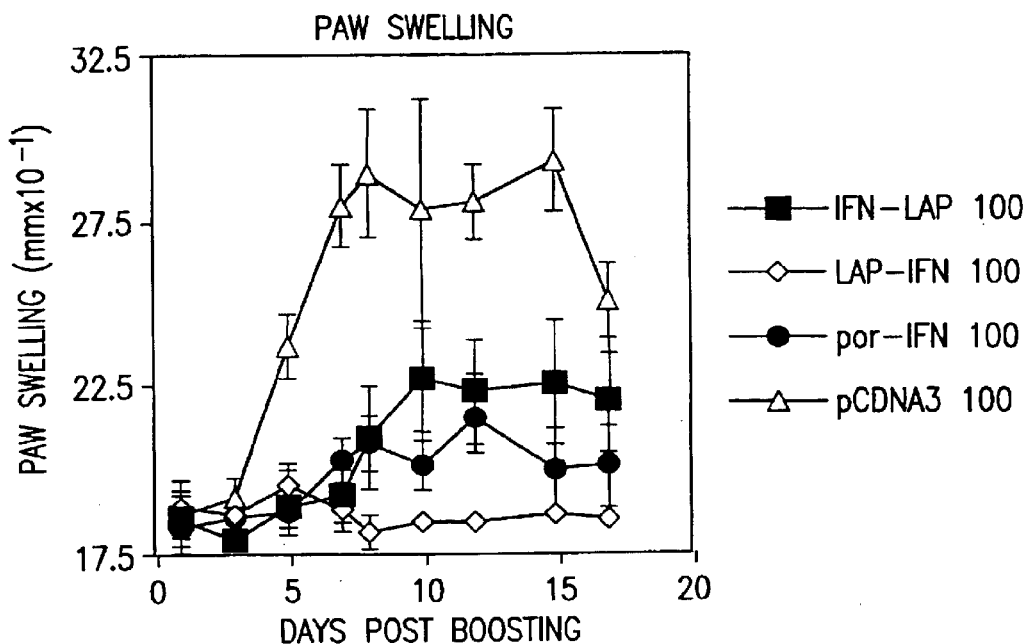
Figure 10B:
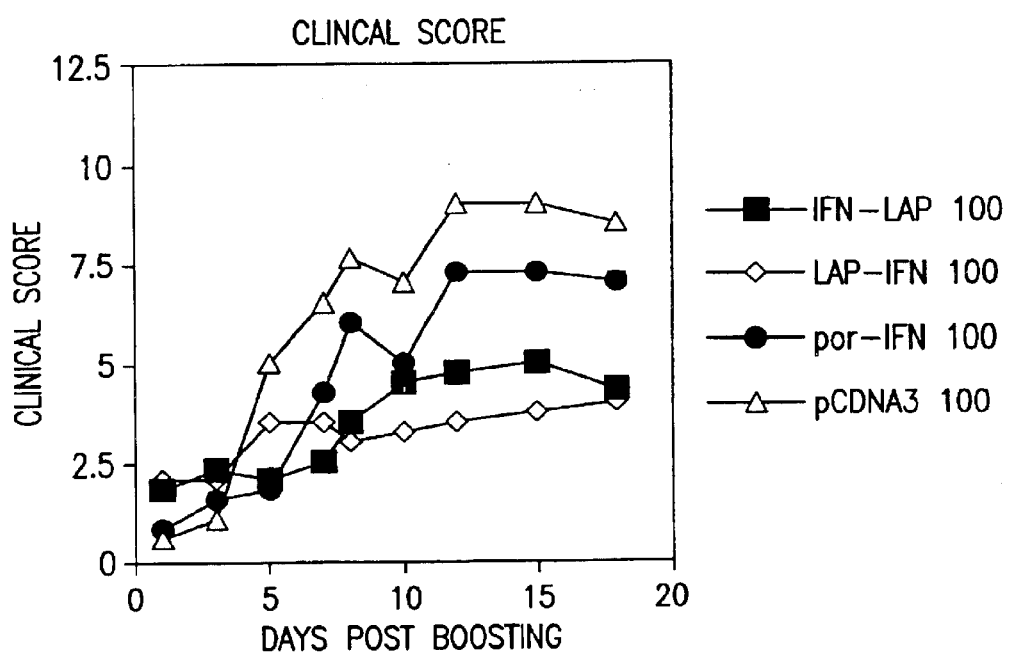

FIGS. 10A and 10B show the inhibition of collagen-induced arthritis by DNA injection with LAP-IFNbeta. Panel shows hind paw swelling and Panel B shows clinical score development from time of boost with collagen type II.

The invention is now described with reference to the following non-limiting examples;

EXAMPLE 1

Construction of LAP-mIFNβ and mIFNβ-LAP

Methods

Cloning of GS-MMP-GS Linker into EcoR1-Not1 Sites of pcDNA3

A vector was constructed by inserting the GS-MMP-GS linker into EcoR1-Not1 cleaved pcDNA3. pcDNA3 is an expression vector (from Invitrogen) which comprises the human cytomegalovirus immediate early promoter and enhancer, together with RNA processing signals allowing transcription.

Double stranded deoxyoligonucleotide coding for the sequence GLY GLY GLY GLY SER PRO LEU GLY LEU TRP ALA GLY GLY GLY SER (SEQ ID NO:1) was designed as follows:

```
Sense oligo:                                (SEQ ID NO:2)
5' AATTCGGGGGAGGCGGATCCCCGCTCGGGCTTTGGGCGGGAGGGGGC
TCAGC 3'

Antisense                                   (SEQ ID NO:3)
oligo:
5' GGCCGCTGAGCCCCCTCCCGCCCAAAGCCCGAGCGGIGGATCCGCCT
CCCCCG 3'
```

Synthetic deoxyoligonucleotides were purchased from Life Technologies Ltd. (Paisley, UK). Annealed deoxyoligonucleotides were cloned into EcoR1-Not1 cleaved pcDNA3 (Invitrogen, Groningen, The Netherlands). The recombinant clone lost its EcoRV site and gained an additional BamH1 site. Plasmid clones were assessed by Southern blot hybridization with end labeled oligos. The clone was referred to as GS-MMP-GS. Restriction enzymes and DNA modifying enzymes were obtained from New England Biolabs, Hitchin, UK.

Construction of LAP (TGFβ) at NH₂ End Followed by GS-MMP-GS and Mature IFNβ

A vector comprising LAP (TGFβ) followed by GS-MMP-GS and mature IFNβ was constructed as follows:

LAP from TGFβ as a 5' unit (with signal peptide) with HindIII and EcoR1 ends was cloned by PCR from plasmid TGFβ-Babe neo (Chernajovsky et al., Gene Ther. 4, 553–559 (1997)). The following primers were used:

```
                                            (SEQ ID NO:4)
Sense       5' CCAAGCTTATGCCGCCCTCCGGGCTGCGG 3'
Primer (SEQ ID NO:5)
Antisense   5' CCGAATTCGCTTTGCAGATGCTGGGCCCT 3'
primer
```

After PCR, the product was phenol extracted, ends filled-in with Klenow and digested with HindIII and EcoR1. The 820 bp product was cloned into GS-MMP-GS plasmid cut with the same enzymes. The clone was referred to as TGFβ-GS-MMP-GS linker. Mature mIFNβ (from mouse) with 5' Not1 and 3' Xba1 sites was synthesized by PCR from clone Aphrodite (Triantaphyllopoulos et al., Gene Ther. 5, 253–263 (1998)) using the following primers:

```
                                            (SEQ ID NO:6)
Sense     5' CGCGGCCGCAATCAACTATAAGCAGCTCCAG 3'
primer (SEQ ID NO:7)
Antisense 5' GGTCTAGATCAGTTTTGGAAGTTTCTGGTAAG 3'
primer
```

After PCR, the fragment was phenol extracted, ends filled-in with Klenow and digested with Not1 and XbaI. The LAP-mIFNβ clone was obtained by cloning the fragment into the Not1 and XbaI sites of TGFβ-GS-MMP-GS linker plasmid. The nucleotide and amino acid sequence of the LAP-mIFNβ insert is shown in FIG. 1.

Construction of mIFNβ at NH₂ End Followed by GS-MMP-GS and Mature LAP (TGFβ)

A vector comprising mature mIFNβ followed by GS-MMP-GS and LAP (TGFβ) was constructed as follows:

Pre-IFNβ with signal peptide and without stop codon was synthesised by PCR as above using the following primers:

```
Sense      5' CCAAGCTTATGAACAACAGGTGGATCCTC 3'    (SEQ ID NO:8)
primer

Antisense  5' CCGAATTCGTTTTGQAAGTTTCTGGTAAG 3'    (SEQ ID NO:9)
primer
```

After PCR synthesis, phenol extraction, filling-in with Klenow fragment of DNA polymerase, the DNA product was digested with HindIII and EcoR1 and cloned into plasmid pCDNA3 GS-MMP-GS in same sites. The clone was referred to as IFNβ-GS-MMP-GS linker. Mature LAP (TGFβ) with stop codon was synthesised by PCR as above using the following primers:

```
Sense      5' CGCGGCCGCACTATCCACCTGCAAGACTATC 3'   (SEQ ID NO:10)
primer

Antisense  5' GGTCTAGATCAGCTTTGCAGATGCTGGGCCCT 3'  (SEQ ID NO:11)
primer
```

After PCR and phenol extraction, the ends were filled-it with Klenow and digested with Not1 and Xba1. The mIFNβ-LAP clone was obtained by cloning the PCR fragment into the same sites of plasmid IFNβ-GS-MMP-GS. The nucleotide and amino acid sequence of the mIFNβ-LAP insert is shown in FIG. 2.

Cloning of Porcine LAP in Front of mIFNβ

Mutated porcine cDNA, mutated at Cys to Ser (223–225), as plasmid pPK14 (Sanderson et al., Proc. Natl. Acad. Sci. USA, 92, 2572–2576 (1995), was kindly provided by P. J. Wirth, NIH, Bethesda, Md. Cloning of porcine LAP was carried out by PCR, using the following set of primers:

Sense primer starting at signal peptide was 5' CGC-CCATGGCGCCTTCGGGGCCT 3' (SEQ ID NO:12). This primer has a modified sequence around the initiator ATG to create a Nco1 site.

Antisense primer 5' CCGAATTCGCTGTGCAGGT-GCTGGGCCCT 3' (SEQ ID NO:13)

Following PCR synthesis, the PCR product was end-filled with Klenow-DNA polymerase, cut with EcoR1, cloned into LAP-mIFNβ plasmid cut with HindIII (filled-in) and then cut with EcoR1 (exchanging human LAP). The construct was named PorcLap-mIFNβ.

Results

Structural Considerations

In order to develop a latent-cytokine using the LAP domain of TGFβ fusion proteins in two conformations, one containing LAP at the amino terminal end of mouse IFNβ (see FIG. 1) and another at its COOH end (see FIG. 2), were constructed.

To avoid processing of the LAP-mIFNβ protein at Arg 278 of LAP, LAP spanning amino acids Met 1 -Ser 273 was cloned. This sequence was followed by a flexible linker (GGGGS, SEQ ID NO:14), a putative MMP9 (Peng et al., Human Gene Therapy, 8, 729–738 (1997); Ye et al., Biochemistry, 34, 4702–4708 (1995)) or putative MMP1 (Nagase and Fields, Biopolymers, 40, 399–416 (1996)) cleavage site (PLGL WA, SEQ ID NO:15) and another flexible portion (GGGGSAAA, SEQ ID NO:16) followed by mature mIFNβ (starting at amino acid Ile-22). Embedding the MMP cleavage site in a hydrophilic area should facilitate access to enzymatic attack. The core of the cleavage site (PLGL, SEQ ID NO:17) has been shown to be cleaved as a peptide by MMP2 and in a different version (PLGI, SEQ ID NO:18) also by MMP3, MMP7 and MMP8 (Nagase and Fields, Biopolymers, 40, 399–416 (1996)).

The IFNβ-LAP molecule consisted of the precursor mIFNβ sequence where its stop codon was mutated to allow read through the flexible linker and MMP site followed by the mature sequence of LAP (from Leu-29 to Ser-273).

The unprocessed LAP-mIFNβ (SEQ ID NO:20) and mIFNβ-LAP (SEQ ID NO:22) fusion proteins have an expected molecular weight of 52,375 and 51,768 Daltons respectively. The primary sequence of these fusion proteins contains four possible N-glycosylation sites. A schematic representation of the primary structure and putative folding of these proteins and their possible interaction with LTBP is shown in FIG. 5. On the right panel of FIG. 5B the folding of LAP-mIFNβ is shown resembling the folding of native TGFβ. Near the amino terminal end (N) of the LAP-mIFNβ, Cys 33 interacts with the third 8-cysteine-rich repeat of LTBP, whilst Cys 224 and 226 are expected to dimerize the protein by intermolecular disulphide bonds (Saharinen et al., Cytokine and Growth Factors, 10, 99–117 (1999)). On the left panel of FIG. 5B, the structure of mIFNβ-LAP is shown. Cys 33 is now located behind the MMP cleavage site and Cys 224 and 226 are closer to the carboxy (C) end of the protein.

EXAMPLE 2

Cell Transfection Studies

Methods

Transfection into DHFR-deficient Chinese Hamster Ovary (CHO) Cells

Dihydrofolate reductase (DHFR)-deficient CHO cells were maintained in HAM-F12 medium (Life Technologies Ltd., Paisley, UK) with 10% fetal bovine serum (FBS) (Life Technologies Ltd.), penicillin/streptomycin and glutamine.

pcDNA3 plasmids (20 μg) expressing LAP-mIFNβ or mIFNβ-LAP were each linearized with PvuI and ligated separately with PvuI cut $pSV_2DHFR$ (1 μg) (Chernajovsky et al., DNA, 3, 297–308 (1984)). After phenol extraction, the plasmids were ligated in 300 μl with T4 DNA ligase at 16° C. for 3 days. The DNA was precipitated in 0.4 M $NH_4$ acetate and resuspended in water to be added as 1 ml calcium phosphate co-precipitate on $0.5\times10^6$ CHO cells on 9 cm plates seeded 24 hrs earlier. 4 hrs later, the cells were treated with 10% glycerol in HAM-F12 without FBS, washed in FBS-free media and left to recover for 48 hrs. Transfected cells were trypsinized and split into six 9 cm plates. Selection was carried out in Alpha-DMEM medium without nucleosides (PAA Laboratories, Linz, Austria), 10% dialyzed FBS (PAA Laboratories) and 1 mg/ml G418 (Geneticin, from Life Technologies Ltd.). Selection media was changed twice a week. Cell clones appeared 2–3 weeks later and were maintained as a population (Chernajovsky et al., DNA, 3, 297–308 (1984)).

For gene amplification, cells were selected additionally with methotrexate (MTX) (Sigma, Poole, UK) at 50 nM (LAP-mIFNβ) or 12.5 nM (mIFNβ-LAP) respectively. Cell clones were isolated by ring cloning and expanded in selection media.

IFNβ Biological Assay

Mouse IFNβ biological activity was assessed by inhibition of the cytopathic effect of EMC virus (kindly provided by I. Kerr, Imperial Cancer Research Fund, London) infection in mouse $LTK^-$ cells using doubling dilutions of cell supernatants as described (Triantaphyllopoulos et al. Gene Ther. 5, 253–263 (1998)). Where indicated, serum-free CHO supernatants were concentrated by centrifugation using Vivaspin filters (Sartorious, Goettingen, Germany) with a cut off of 30,000 kDa.

Metabolic Labelling of CHO Cells Confluent plates of permanently transfected cells or non-transfected CHO cells were washed with cysteine-methionine free medium (Life Technologies Ltd.) containing 10% dialyzed FBS and supplemented with thymidine, glutamine, penicillin/streptomycin and 150 µg/ml L-proline. Labelling was either overnight or for 48 hrs in the presence of $^{35}$S-methionine-cysteine mix (Amersham-Pharmacia Biotech, Bucks, UK) at 1 Ci/mmol using 250 mCi/plate in 5 ml media.

At the end of the labelling period, supernatants were collected, cell debris spun down and clear supernatants supplemented where indicated with serine-protease inhibitors (SPI) (pepstatin-A at 10 µg/ml, aprotinin at 1 µg/ml, chymostatin at 10 µg/ml, leupeptin at 10 µg/ml and AEBSF (4-(2-aminoethyl)benzene sulphonyl-fluoride, HCl) at 200 µM (all from Calbiochem, Beeston, UK). These supernatants were frozen at −70° C. until used for immunoprecipitation studies.

Immunoprecipitation

Supernatants from metabolically labelled cells were pre-cleared with (400 µl) Protein-G-Sepharose (Amersham Pharmacia Biotech) equilibrated in PBS with 0.1% NP40 (50% beads/vol) (BDH, Poole, UK). Supernatants containing 25×10$^6$ cpm of trichloroacetic acid (TCA) (Sigma) total precipitated protein were used (approximately 5–7 ml of cell supernatants). After end-over-end mixing for 4 hrs at 4° C., protein-G Sepharose was removed by centrifugation (2000 RPM, 5 min). The cleared supernatant was incubated with either goat-anti-human-LAP antibody (R&D Systems, Oxon, UK at 0.9 µg/ml), or monoclonal rat-anti-mIFNβ (7F-D3, AMS, Abingdon, UK, at a dilution of 1/250) for 3–4 hrs at 4° C.

The antigen-antibody complexes were then bound to Protein-G-Sepharose (700 µl of 50% solution) by mixing overnight at 4° C. rolling end-over-end. Protein-G-Sepharose beads were washed three times with 5 ml 0.1% NP40 in PBS. Proteins bound to beads were split into fractions of 50 µl beads in small tubes and either directly resuspended in Laemmli-loading buffer or used in MMPs reactions prior to SDS-PAGE in 10% acrylamide gel. Alternatively, supernatants were treated with MMPs and then immunoprecipitated. Gels were fixed for 30 min. in 7% acetic acid and 10% methanol and treated with 1 M sodium salicylate before drying and exposing to autoradiography with X-ray film. Coloured protein molecular weight markers were from Amersham-Pharmacia Biotech.

Supernatants from MTX selected cells were treated with MMPs or synovial fluid from rheumatoid arthritis patients (RA/SF: 1/5) overnight, the reactions stopped with 10 mM EDTA and then immunoprecipitated.

MMP Digestion

Recombinants pro-MMP9 (kindly provided by R. Fridman, Wayne University, Detroit) or active MMP1 and MMP3 (kindly provided by H. Nagase, Kennedy Institute of Rheumatology, London) were incubated overnight at 37° C. with immunoprecipitated supernatants from CHO cells in 2 mM TrisHCl pH 7.4, 5 mM CaCl$_2$, 140 mM NaCl and 0.1% Brij 35 (all from Sigma) in 50 µl at 1 µg/ml or were directly added to cell supernatants (at 4 µg/ml) Aminophenylmercuric acetate (APMA) (Sigma) at 10 µmM was used in certain experiments to activate pro-MMP9 overnight at 37° C. (Ogata et al., J. Biol. Chem. 270, 18506–18511 (1995)).

Results

TABLE 1

Biological assay of mIFNβ

| Sample | Antiviral activity (U/ml) |
|---|---|
| Non transfected | 0 |
| mIFNβ-LAP | 210 |
| LAP-mIFNβ | 0 |

Mean value of triplicate assay

LAP-mIFNβ and mIFNβ-LAP recombinant proteins were expressed in dihydrofolate reductase deficient chinese hamster ovary (DHFR$^-$ CHO) cells (clone CHO-K1) after permanent co-transfection of linearized plasmids with the DHFR plasmid (pSV$_2$DHFR) (Chernajovsky et al., DNA, 3, 297–308 (1984)) and selection both in G418 and dialyzed serum.

As shown in Table 1, mIFNβ-LAP was secreted having a low residual biological activity whilst LAP-mIFNβ was completely "latent" or inactive. The level of protein expression was similar as confirmed by western blotting with an anti-LAP antibody (not shown).

Biochemical Characterization of Recombinant Proteins

Secreted proteins from permanently transfected cells were metabolically labeled with $^{35}$S-methionine and cysteine. Both LAP-mIFNβ and mIFNβ-LAP labeled proteins showed two major bands above 97 kDa in non-reducing conditions that were not seen in supernatants from CHO non-transfected cells (FIG. 6).

Upon immunoprecipitation with anti-LAP antibody, LAP-mIFNβ and mIFNβ-LAP supernatants showed three bands one at 57 kDa another at 135 kDa and another minor component at around 75 kDa in reducing conditions FIG. 7. The 135 kDa protein is probably the CHO-derived (LTBP) which is di-sulphide linked to LAP (Saharinen et al., Cytokine and Growth Factors, 10, 99–117 (1999)).

The minor 75 kDa component (FIG. 7 lanes 1, 3 and 5) becomes the major component recognised by anti-LAP antibody upon gene amplification with MTX (FIG. 8A, lanes 1–4). Interestingly, the monoclonal anti-mIFNβ antibody does not seem to recognize the 75 kDa glycosylated product (FIG. 8A and 7, lanes 5–8) and the anti-LAP poorly recognizes it in the mIFNβ-LAP configuration (FIG. 8A, lanes 5–8) of the protein indicating that the fusion proteins have different conformations. Similar results were obtained when the immunoprecipitated material was treated enzymatically (with MMP1 or MMP3) and then separated on SDS-PAGE. The difference in conformation may explain the different sensitivity of these proteins to different MMPs (see below) and their degree of latency.

The predicted molecular weight of the secreted recombinant proteins is 49,376 Da for both LAP-mIFNβ and mIFNβ-LAP. The increased molecular weight determined, may be due to glycosylation of these proteins. Incubation of immunoprecipitated proteins with N-glycosidase F, yields two major proteins of molecular weights 70 kDa and 51 kDa which correspond to LTBP and fusion protein respectively (not shown).

MMP Cleavage of Recombinant Proteins

Immunoprecipitated complexes were treated overnight with single MMPs or their combination. As shown in FIG. 7, pro-MMP9 or MMP1 did not cleave very efficiently the 57 kDa recombinant product. MMP1 was capable of cleaving the glycosylated form of the fusion protein (FIG. 7, lanes 3 and 4; FIG. 8A , lane 2) whilst MMP3 was capable on its own to digest it into several discreet bands FIG. 7 lanes 5 and 6; FIGS. 8A and 8B, lanes 3 and 7).

The LTBP band was also cleaved by MMP3 (FIG. 7, lane 3 and 4 and FIG. 8B, lanes 3 and 7) giving rise to a 78 kDa product. Two of the digested products (MW 36 kda and 20 kDa) correspond to the expected LAP and IFNβ polypeptide fragments respectively.

The specificity shown in these in vitro experiments may not fully reflect the antiviral activity measured in cell supernatants following MMP treatment. Cell supernatants were already activated to a certain extent indicating that other proteolytic enzymes present in the supernatant may activate the latent-cytokine moiety. Increased proteolysis of the fusion polypeptides after immunoprecipitation using a combination of recombinant pro-MMP9 with MMP1 or MMP3, or with APMA-activated pro-MMP9 on its own in vitro (not shown) was not apparent.

Activation of Latent IFNβ by MMPs

TABLE 2 mIFNβ biological activity (U/ml) from concentrated supernatants treated with MMPs

|  |  | pro-MMP9 | MMP1 | MMP3 | pro-MMP9 + MMP1 | pro-MMP9 + MMP3 |
|---|---|---|---|---|---|---|
| mIFNβ-LAP | Exp.1 | 1,305 | 1,740 | 870 | 3,481 | 7,740 |
| LAP-mIFNβ | Exp.1 | 163 | 217 | 109 | 435 | 217 |
|  | Exp.2 | 109 | N.D. | N.D. | 435 | 217 |

Concentrated serum-free supernatants were treated with MMPs as shown.
N.D. = not done

TABLE 3 mIFNβ biological activity (U/ml) from non-concentrated supernatants from MTX-amplified CHO- transfected cells.

TREATMENT

|  | none | MMP1 | MMP3 | pro-MMP9 | pro-MMP9 + MMP1 | pro-MMP9 + MMP3 | RA-S.F. | no SPI. |
|---|---|---|---|---|---|---|---|---|
| LAP-mIFN (50 nM MTX) | 288 | 6144 | 9216 | 288 | 1536 | 768 | 1152 | 768 |
| mIFNβ-LAP (12.5 nM MTX) | 1536 | 6144 | 3072 | 1536 | 1536 | 4608 | 6144 | 3072 |

Supernatants were supplemented with or without (last row) serine protease inhibitors (SPI) and MMPs as indicated. The RA.SF is the same used also in FIG. 6.

The non-concentrated supernatant had approximately 210 U/ml of antiviral activity corresponding to about 0.3 ng protein (Iwakura et al., J. Biol. Chem. 253, 5074–5079 (1978)). Cell supernatants were concentrated 100 fold by centrifugation through porous membranes in order to allow for MMP activity at a higher substrate concentration.

Upon concentration, even the LAP-IFNβ supernatant demonstrated antiviral activity without any further treatment (Table 3). This result may be explained by the fact that CHO cells are reported to secrete a variety of proteinases (Goldman et al., Cytotechnology, 23, 103–111 (1997); Satoh et al., Cytotechnology, 13, 79–88 (1993)) including MMPs (Masure et al., Eur. J. Biochem. 244, 21–30 (1997). Possibly, some natural inhibitors of MMPs (TIMPs) may be removed from the proteinases by this concentration method facilitating their activity.

Supernatants from non-transfected CHO cells had no biological activity even after treatment with MMP's or rheumatoid arthritis synovial fluid (RA-S.F) at 1/5 of final volume (data not shown).

Addition of MMP1 to concentrated supernatants slightly increased the biological activity whilst addition of both MMP1 and pro-MMP9 or MMP3 and pro-MMP9 did the same (see Table 2). Interestingly, treatment of IFNβ-LAP with MMP1 and pro-MMP9 lead to a 3–6 fold increase in antiviral activity indicating that further activation of this molecule may be obtained.

Using non-concentrated supernatants from MTX amplified cells, it was demonstrated that both MMP1 and MMP3 can activate LAP-IFNβ by 21 and 32 fold respectively (Table 3), and that synovial fluid from rheumatoid arthritis patients can activate it up to 4 fold (Table 3). mIFNβ-LAP can also be activated but as previously shown (Table 1) its level of basal activity is high. FIGS. 8A and 8B (lanes 4 and 8) show that synovial fluid from rheumatoid arthritis patients can also cleave the fusion proteins to discrete products of 36 kDa and 20 kDa corresponding to LAP and IFNβ respectively.

As mentioned above, incubation of the supernatants without protease inhibitors yields increased biological activity, indicating that secreted enzymes from the CHO cells may cleave it. The sensitivity of the two fusion proteins to the presence of MMP9 is different showing that mIFNβ-LAP may be activated whilst for LAP-IFNβ, MMP9 appears inhibitory, perhaps inducing its further degradation by other enzymes present in the CHO cell supernatants.

Activation of Latent IFNβ with Samples from Inflamed Sites

FIG. 8 and Table 3 showed that synovial fluid from rheumatoid arthritis patients is capable of activating the latent cytokine.

To assess whether long term incubation of the latent cytokine with these samples may lead to its degradation or accumulation into active compound, both LAP-mIFNβ and mIFNβ-LAP were incubated for up to five days at 37° C. in the presence or absence of synovial fluid from rheumatoid arthritis patients and then applied to the IFN biological assay. Empty symbols are samples incubated in medium with 10% FBS whilst filled symbols are samples incubated with 1/5 of vol/vol of rheumatoid arthritis synovial fluid (RA.SF).

Samples were taken at 24 hrs intervals. FIG. 9 shows that incubation over is extended period resulted in increased activity i.e. activation of the LAP-mIFNβ up to 10 fold during the first 24–48 hrs with a steady decrease afterwards. The mIFNβ-LAP failed to be activated and only a decrease in its activity was seen. This result clearly indicates that the LAP-IFNβ conformation can have potential therapeutic uses.

No activation was seen using mIFNβ-LAP. Overall, in both cases the protein activity decreased over time as proteases found in the medium of the cells are capable of degrading the engineered proteins.

To determine whether activation of the latent cytokine could be corroborated by using samples from another pathological inflammatory condition, cerebrospinal fluid from experimental allergic encephalomyelitis monkeys were tested. After overnight incubation, two out of the three samples tested increased the biological activity of the fusion proteins up to four times higher than their parallel serum samples (data not shown), indicating that site-specific activation may be obtainable.

EXAMPLE 3

In order to assess whether the latency detected with LAP-mIFNβ required the formation of a putative closed shell structure bounded by the dimeric disulphide linked LAP, a fusion protein was constructed using the porcine LAP that was mutated in Cys 223 and 225 to Ser.

Methods

Preparation of Construct

Porcine LAP was cloned by PCR as set out in Example 1. The primers used were as set out in Example (cloning of porcine LAP). The cloned porcine LAP was mutated in Cys 223 and 225 to Ser (Sanderson et al., Proc. Natl. Acad. Science, 92, 2572–2576 (1995)).

Transient Transfection Monkey COS-7 Cells

20 μg plasmid DNA, PorcLAP-mIFNβ and mIFNβ-LAP & LAP-mIFNβ controls, were transfected by the calcium phosphate precipitation method in duplicates to 0.5×106 COS-7 cells seeded in 9 cm plates as described above. The DNA co-precipitate was left on the cells overnight instead of 4 hrs. COS-7 cells were grown in DMEM with antibiotics and 10% FBS. 48 hrs after glycerol shock the supernatants were collected for IFN antiviral assay.

Results

The mutated construct PorcLAP-mIFNβ was compared to the other constructs for its biological activity in vitro following transient transfection to COS-7 cells. Table 4 shows that PorcLAP-mIFNβ was as active as mIFNβ-LAP in this assay demonstrating that.

TABLE 4

| Plasmid | Antiviral activity (U/ml) |
| --- | --- |
| LAP-mIFNβ | 0 |
| PorcLAP-mIFNβ | 256 |
| mIFNβ-LAP | 256 |

Results shown are representative of one of two experiments.

Conclusion

The results show that disulphide bonds at positions 223 and 225 are required for latency of LAP-mIFNβ.

EXAMPLE 4

Cloning and Expression of Human IFNβ, IL-2 and IL-10-LAP Fusion Proteins

Construction of Human IFNβ-MMP-LAP and LAP-MMP-human IFNβ will facilitate testing of the expression of these constructs in CHO cell lines and subsequent testing of the activity of the expressed product with some human cell lines in vitro and in vivo.

Constructs comprising human IL-2 and IL-10 will be expressed and tested as above. Purification of the expressed fusion proteins will utilise a poly His tail as an anchor for purification schemes. Such purification schemes are well known in the art.

EXAMPLE 5

Collagen Induced Arthritis (CIA) and DNA Injection

DBA/1 mice were immunised with collagen type II (CII) as described in Dreja, et al. Arthritis and Rheumatism, 43, 1698–1708 (2000) and 3 weeks later were boosted with CII in incomplete Freund's adjuvant. 100 micrograms plasmid DNA in PBS was injected intramuscularly at 3 sites in the qudriceps, on the day of arthritis onset and mice were scored every other day for clinical arthritis and hind paw swelling was measured with calipers as described (Dreja, et al. Arthritis and Rheumatism, 43, 1698–1708, (2000)).

In an arthritis model (CIA), the relative effectiveness of the latent cytokine (LAP-mIFNβ) versus the active versions (PorcLAP-mIFNβ and mIFNβ-LAP) was measured. The latent LAP-mIFNb shows greater efficacy than either of the active moieties, mIFNb-LAP or PorcLAP-IFNb, as compared with the control treat with pCDNA3 empty plasmid vector.

It was found that when delivered by gene therapy by intramuscular injection the latent cytokine was more efficacious in the treatment of established disease.

Conclusions

It has been shown herein that an active cytokine molecule could be designed to become "latent" by addition of the latency domain of TGFβ either at its $NH_2$ or COOH termini. The cytokine IFNβ was used in the experimental models.

The LAP domain of TGFβ conferred "latency" to IFNβ which could be abrogated by incubating the fusion protein with MMPs. Possibly the latency has to do with steric hindrance by LAP on the interaction between the IFNβ moiety with its cellular receptors. Despite the fact that both $NH_2$ and COOH ends of the molecule are in close proximity in the crystal structure of IFNβ, a better 'shell' appeared to be conferred by fusing the LAP domain at its $NH_2$ terminus as it is found in TGFβ itself. It is plausible that with other cytokines this may be different, depending on their tertiary structure and the surface of interaction with their receptors.

The MMP site located between LAP and IFNβ could be cleaved in vitro by MMP-3 and MMP-1. MMP-3 and MMP-1 have homologous regions in their active site (Massova et al., J. Mol. Model. 3, 17–30 (1997)). It is quite plausible that other MMPs will also cleave this site as shown by the activation occurring in concentrated serum-free supernatants of CHO cells (Table 2). Expression of MMPs is very tightly regulated (Han et al., Autoimmunity, 28, 197–208 (1998)). MMPs are active during tissue remodelling, wound healing and inflammation (Kubota et al., J. Oral & Maxillofacial Surgery, 55, 20–27 (1997); Van Meurs et. al., Arthritis & Rheumatism, 42, 2074–2084 (1999); Leppert et al., Brain, 121, 2327–2334 (1998); Uhm et al., Annals of Neurology, 46, 319–324 (1999); Louis et al., Clin. Exp. Immunol. 120, 241–246 (2000); Baugh et al., Gastroenterology, 117 814–822 (1999)). MMPs are also necessary for tumour cells to invade surrounding tissue. Indeed expression of tissue inhibitor of metalloproteases (TIMPs) can inhibit tumour invasion and metastasis (DeClerck et al., Cancer Res. 52, 701–708 (1992)).

MMP9 could not cleave the fusion proteins. Using fluorogenic peptide substrates wit the sequence PLGLWA-d-R the value of rate of hydrolysis (kcat/Km) of matrix metalloproteinases appear to follow the order MMP9>MMP2>MMP7>MMP3>MMP1 (Nagase and Fields, Biopolymers, 40, 399–416 (1996)). This discrepancy in hydrolysis sensitivity between the peptide substrate and the engineered proteins used in this study may be related to their tertiary structure.

The "latent" cytokine design appears to have several advantages. Firstly, upon administration the cytokine, it does not appear to be rapidly taken up by cells bearing its receptors, this may have impact on its toxicity and may provide for a longer half-life. LAP-containing TGFβ has been shown to have an increased half-life in vivo Wakefield et al., J. Clin. Invest. 86, 1976–1984 (1990)). Thus, as a consequence, therapeutic systemic administration could be dosed at lower concentrations.

Secondly, both LAP and LTBP may facilitate the interaction of the latent cytokine with the extracellular matrix.

Thirdly, the cytokine may not typically be released to interact with cellular receptors unless inflammatory or tissue remodelling processes are taking place involving MMP activity. Such activity is found in osteoarthritis, rheumatoid arthritis (Kubota et al., J. Oral & Maxillofacial Surgery, 55, 20–27 (1997): Van Meurs et al., Arthritis & Rheumatism, 42, 2074–2084 (1999); Singer et al., Osteoarthritis & Cartilage, 5, 407–418 (1997)) and other types of chronic disease such as inflammatory bowel disease (Loius et al., Clin. Exp. Immunol, 120, 241–246 (2000); Baugh et al., Gastroenterology, 117, 814–822 (1999)), multiple sclerosis (Leppert et al., Brain, 121, 2327–2334)), atherosclerosis (Libby, Vascular Medicine, 3, 225–229 (1998)) and during cancer invasion (DeClerek et al., Cancer Res. 52, 701–708 (1992)).

It could be argued that upon cleavage, the release of LAP could have antagonistic effects for TGFβ, as it has been shown that in vitro LAP is capable of inhibiting active TGFβ action (Wakefield et al., Growth Factors, 1, 203–218 (1989)). However, it is expected that our LAP-fusion protein may exert its action at sites of inflammation where free radicals abound. It has been shown that nitrosylation of LAP disables its capacity for binding to TGFβ (Vodovotz et al., Cancer Res. 59, 2142–2149 (1999)). Thus it is unlikely that in sites of inflammation the released LAP will antagonise TGFβ function.

Additional modifications to the MMP cleavage site may provide for additional tissue specificity.

What is claimed is:

1. A method of treating inflammatory disease in a patient comprising administering to said patient a therapeutically effective amount of a fusion protein comprising a latency associated peptide and a proteolytic cleavage site, wherein said fusion protein is covalently linked to an interleukin selected from the group consisting of interleukin-4, interleukin-5, interleukin-6, interleukin-10, interleukin-11, interleukin-12 and interleukin-13 and wherein said fusion protein is heterologous to said interleukin.

2. The method of claim 1, wherein the latency associated peptide comprises the precursor peptide of TGFβ-1, 2, 3, 4 or 5.

3. The method of claim 1, wherein the proteolytic cleavage site is a matrix metalloproteinase (MMP) cleavage site.

4. The method of claim 1, wherein the fusion protein is covalently linked to the latent TGFβ binding protein (LTBP).

5. The method of claim 1, wherein the inflammatory disease is selected from the group consisting of osteoarthritis, scleroderma, renal disease, rheumatoid arthritis, inflammatory bowel disease, multiple sclerosis and atherosclerosis.

6. The method of claim 1, wherein said interleukin is interleukin-4.

7. A method for providing latency to an interferon comprising covalently linking a fusion protein comprising a latency associated peptide and a proteolytic cleavage site with the interferon, wherein said fusion protein is heterologous to said interferon and wherein said fusion protein provides latency to said interferon.

8. The method of claim 7, wherein the latency associated peptide comprises the precursor peptide of TGFβ-1, 2, 3, 4 or 5.

9. The method of claim 7, wherein the proteolytic cleavage site is a matrix metalloproteinase (MMP) cleavage site.

10. The method of claim 7, wherein the fusion protein is covalently linked to the latent TGFβ binding protein (LTBP).

11. The method of claim 7, wherein said interferon is interferon-β.

12. A method for providing latency to an interleukin comprising covalently linking a fusion protein comprising a latency associated peptide and a proteolytic cleavage site with the interleukin, wherein said fusion protein is heterologous to said interleukin and wherein said fusion protein provides latency to said interleukin.

13. The method of claim 12, wherein the latency associated peptide comprises the precursor peptide of TGFβ-1, 2, 3, 4 or 5.

14. The method of claim 12, wherein the proteolytic cleavage site is a matrix metalloproteinase (MMP) cleavage site.

15. The method of claim 12, wherein the fusion protein is covalently linked to the latent TGFβ binding protein (LTBP).

16. The method of claim 12, wherein said interleukin is selected from the group consisting of interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20 and interleukin-21.

17. The method of claim 16, wherein said interleukin is selected from the group consisting of interleukin-2 and interleukin-4.

18. A method of treating inflammatory disease in a patient comprising administering to said patient a therapeutically effective amount of a fusion protein comprising a latency associated peptide and a proteolytic cleavage site, wherein said fusion protein is covalently linked to an interferon selected from the group consisting of interferon-α and interferon-β, and wherein said fusion protein is heterologous to said interferon.

19. The method of claim 18, wherein the latency associated peptide comprises the precursor peptide of TGFβ-1, 2, 3, 4 or 5.

20. The method of claim 18, wherein the proteolytic cleavage site is a matrix metalloproteinase (MMP) cleavage site.

21. The method of claim 18, wherein the fusion protein is covalently linked to the latent TGFβ binding protein (LTBP).

22. The method of claim 18, wherein the inflammatory disease is selected from the group consisting of osteoarthritis, scleroderma, renal disease, rheumatoid arthritis, inflammatory bowel disease, multiple sclerosis and atherosclerosis.

23. The method of claim 18, wherein said interferon is interferon-β.

* * * * *

SEQUENCE LISTING

<160> NUMBER OF SEQ ID NOS: 100

<210> SEQ ID NO 1
<211> LENGTH: 15
<212> TYPE: PRT
<213> ORGANISM: Artificial Sequence
<220> FEATURE:
<223> OTHER INFORMATION: MMP cleavage site including linker sequence

<400> SEQUENCE: 1

Gly Gly Gly Gly Ser Pro Leu Gly Leu Trp Ala Gly Gly Gly Ser
1               5                   10                  15

<210> SEQ ID NO 2
<211> LENGTH: 52
<212> TYPE: DNA
<213> ORGANISM: Artificial Sequence
<220> FEATURE:
<223> OTHER INFORMATION: Sense oligo

<400> SEQUENCE: 2
aattcggggg aggcggatcc ccgctcgggc tttgggcggg aggggggctca gc        52

<210> SEQ ID NO 3
<211> LENGTH: 52
<212> TYPE: DNA
<213> ORGANISM: Artificial Sequence
<220> FEATURE:
<223> OTHER INFORMATION: Antisense oligo

<400> SEQUENCE: 3
ggccgctgag ccccctcccg cccaaagccc gagcggggat ccgcctcccc cg        52

<210> SEQ ID NO 4
<211> LENGTH: 29
<212> TYPE: DNA
<213> ORGANISM: Artificial Sequence
<220> FEATURE:
<223> OTHER INFORMATION: Sense Primer

<400> SEQUENCE: 4
ccaagcttat gccgccctcc gggctgcgg                                   29

<210> SEQ ID NO 5
<211> LENGTH: 29
<212> TYPE: DNA
<213> ORGANISM: Artificial Sequence
<220> FEATURE:
<223> OTHER INFORMATION: Antisense Primer

<400> SEQUENCE: 5
ccgaattcgc tttgcagatg ctgggccct                                29

<210> SEQ ID NO 6
<211> LENGTH: 31
<212> TYPE: DNA
<213> ORGANISM: Artificial Sequence
<220> FEATURE:
<223> OTHER INFORMATION: Sense Primer

<400> SEQUENCE: 6
cgcggccgca atcaactata agcagctcca g                             31

<210> SEQ ID NO 7
<211> LENGTH: 32
<212> TYPE: DNA
<213> ORGANISM: Artificial Sequence
<220> FEATURE:
<223> OTHER INFORMATION: Antisense Primer

<400> SEQUENCE: 7
ggtctagatc agttttggaa gtttctggta ag                            32

<210> SEQ ID NO 8
<211> LENGTH: 29
<212> TYPE: DNA
<213> ORGANISM: Artificial Sequence
<220> FEATURE:
<223> OTHER INFORMATION: Sense Primer

<400> SEQUENCE: 8
ccaagcttat gaacaacagg tggatcctc                                29

<210> SEQ ID NO 9
<211> LENGTH: 29
<212> TYPE: DNA
<213> ORGANISM: Artificial Sequence
<220> FEATURE:
<223> OTHER INFORMATION: Antisense Primer

<400> SEQUENCE: 9
ccgaattcgt tttggaagtt tctggtaag                                29

<210> SEQ ID NO 10
<211> LENGTH: 31
<212> TYPE: DNA
<213> ORGANISM: Artificial Sequence
<220> FEATURE:
<223> OTHER INFORMATION: Sense Primer

<400> SEQUENCE: 10
cgcggccgca ctatccacct gcaagactat c                             31

<210> SEQ ID NO 11
<211> LENGTH: 32
<212> TYPE: DNA
<213> ORGANISM: Artificial Sequence
<220> FEATURE:
<223> OTHER INFORMATION: Antisense Primer

```
<400> SEQUENCE: 11
ggtctagatc agctttgcag atgctgggcc ct                                32

<210> SEQ ID NO 12
<211> LENGTH: 23
<212> TYPE: DNA
<213> ORGANISM: Artificial Sequence
<220> FEATURE:
<223> OTHER INFORMATION: Sense Primer

<400> SEQUENCE: 12
cgcccatggc gccttcgggg cct                                          23

<210> SEQ ID NO 13
<211> LENGTH: 29
<212> TYPE: DNA
<213> ORGANISM: Artificial Sequence
<220> FEATURE:
<223> OTHER INFORMATION: Antisense Primer

<400> SEQUENCE: 13
ccgaattcgc tgtgcaggtg ctgggccct                                    29

<210> SEQ ID NO 14
<211> LENGTH: 5
<212> TYPE: PRT
<213> ORGANISM: Artificial Sequence
<220> FEATURE:
<223> OTHER INFORMATION: Flexible linker

<400> SEQUENCE: 14

Gly Gly Gly Gly Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Cleavage site

<400> SEQUENCE: 15

Pro Leu Gly Leu Trp Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Flexible portion

<400> SEQUENCE: 16

Gly Gly Gly Gly Ser Ala Ala Ala
1               5

<210> SEQ ID NO 17
<211> LENGTH: 4
<212> TYPE: PRT
<213> ORGANISM: Artificial Sequence
<220> FEATURE:
<223> OTHER INFORMATION: Core of cleavage site

<400> SEQUENCE: 17

Pro Leu Gly Leu
1
```

<210> SEQ ID NO 18
<211> LENGTH: 4
<212> TYPE: PRT
<213> ORGANISM: Artificial Sequence
<220> FEATURE:
<223> OTHER INFORMATION: Core of cleavage site

<400> SEQUENCE: 18

Pro Leu Gly Ile
1

<210> SEQ ID NO 19
<211> LENGTH: 1376
<212> TYPE: DNA
<213> ORGANISM: Artificial Sequence
<220> FEATURE:
<223> OTHER INFORMATION: LAP-mIFNbeta construct
<221> NAME/KEY: CDS
<222> LOCATION: (1)..(1368)

<400> SEQUENCE: 19

```
atg ccg ccc tcc ggg ctg cgg ctg ctg ccg ctg ctg cta ccg ctg ctg      48
Met Pro Pro Ser Gly Leu Arg Leu Leu Pro Leu Leu Leu Pro Leu Leu
1               5                   10                  15 tgg cta ctg gtg ctg acg cct ggc ccg ccg gcc gcg gga cta tcc acc      96
Trp Leu Leu Val Leu Thr Pro Gly Pro Pro Ala Ala Gly Leu Ser Thr
            20                  25                  30 tgc aag act atc gac atg gag ctg gtg aag cgg aag cgc atc gag gcc     144
Cys Lys Thr Ile Asp Met Glu Leu Val Lys Arg Lys Arg Ile Glu Ala
        35                  40                  45 atc cgc ggc cag atc ctg tcc aag ctg cgg ctc gcc agc ccc cgg agc     192
Ile Arg Gly Gln Ile Leu Ser Lys Leu Arg Leu Ala Ser Pro Pro Ser
    50                  55                  60 cag ggg gag gtg ccg ccc ggc ccg ctg ccc gag gcc gtg ctc gcc ctg     240
Gln Gly Glu Val Pro Pro Gly Pro Leu Pro Glu Ala Val Leu Ala Leu
65                  70                  75                  80 tac aac agc acc cgc gac cgg gtg gcc ggg gag agt gca gaa ccg gag     288
Tyr Asn Ser Thr Arg Asp Arg Val Ala Gly Glu Ser Ala Glu Pro Glu
                85                  90                  95 ccc gag cct gag gcc gac tac tac gcc aag gag gtc acc cgc gtg cta     336
Pro Glu Pro Glu Ala Asp Tyr Tyr Ala Lys Glu Val Thr Arg Val Leu
            100                 105                 110 atg gtg gaa acc cac aac gaa atc tat gac aag ttc aag cag agt aca     384
Met Val Glu Thr His Asn Glu Ile Tyr Asp Lys Phe Lys Gln Ser Thr
        115                 120                 125 cac agc ata tat atg ttc ttc aac aca tca gag ctc cga gaa gcg gta     432
His Ser Ile Tyr Met Phe Phe Asn Thr Ser Glu Leu Arg Glu Ala Val
    130                 135                 140 cct gaa ccc gtg ttg ctc tcc cgg gca gag ctg cgt ctg ctg agg agg     480
Pro Glu Pro Val Leu Leu Ser Arg Ala Glu Leu Arg Leu Leu Arg Arg
145                 150                 155                 160 ctc aag tta aaa gtg gag cag cac gtg gag ctg tac cag aaa tac agc     528
Leu Lys Leu Lys Val Glu Gln His Val Glu Leu Tyr Gln Lys Tyr Ser
                165                 170                 175 aac aat tcc tgg cga tac ctc agc aac cgg ctg ctg gca ccc agc gac     576
Asn Asn Ser Trp Arg Tyr Leu Ser Asn Arg Leu Leu Ala Pro Ser Asp
            180                 185                 190 tcg cca gag tgg tta tct ttt gat gtc acc gga gtt gtg cgg cag tgg     624
Ser Pro Glu Trp Leu Ser Phe Asp Val Thr Gly Val Val Arg Gln Trp
        195                 200                 205 ttg agc cgt gga ggg gaa att gag ggc ttt cgc ctt agc gcc cac tgc     672
```

```
                                                                              720
tcc tgt gac agc agg gat aac aca ctg caa gtg gac atc aac ggg ttc
Ser Cys Asp Ser Arg Asp Asn Thr Leu Gln Val Asp Ile Asn Gly Phe
225             230                 235                 240

768
act acc ggc cgc cga ggt gac ctg gcc acc att cat ggc atg aac cgg
Thr Thr Gly Arg Arg Gly Asp Leu Ala Thr Ile His Gly Met Asn Arg
            245                 250                 255

816
cct ttc ctg ctt ctc atg gcc acc ccg ctg gag agg gcc cag cat ctg
Pro Phe Leu Leu Leu Met Ala Thr Pro Leu Glu Arg Ala Gln His Leu
        260                 265                 270

864
caa agc gaa ttc ggg gga ggc gga tcc ccg ctc ggg ctt tgg gcg gga
Gln Ser Glu Phe Gly Gly Gly Gly Ser Pro Leu Gly Leu Trp Ala Gly
    275                 280                 285

912
ggg ggc tca gcg gcc gca atc aac tat aag cag ctc cag ctc caa gaa
Gly Gly Ser Ala Ala Ala Ile Asn Tyr Lys Gln Leu Gln Leu Gln Glu
290                 295                 300

960
agg acg aac att cgg aaa tgt cag gag ctc ctg gag cag ctg aat gga
Arg Thr Asn Ile Arg Lys Cys Gln Glu Leu Leu Glu Gln Leu Asn Gly
305             310                 315                 320

1008
aag atc aac ctc acc tac agg gcg gac ttc aag atc cct atg gag atg
Lys Ile Asn Leu Thr Tyr Arg Ala Asp Phe Lys Ile Pro Met Glu Met
                325                 330                 335

1056
acg gag aag atg cag aag agt tac act gcc ttt gcc atc caa gag atg
Thr Glu Lys Met Gln Lys Ser Tyr Thr Ala Phe Ala Ile Gln Glu Met
            340                 345                 350

1104
ctc cag aat gtc ttt ctt gtc ttc aga aac aat ttc tcc agc act ggg
Leu Gln Asn Val Phe Leu Val Phe Arg Asn Asn Phe Ser Ser Thr Gly
        355                 360                 365

1152
tgg aat gag act att gtt gta cgt ctc ctg gat gaa ctc cac cag cag
Trp Asn Glu Thr Ile Val Val Arg Leu Leu Asp Glu Leu His Gln Gln
    370                 375                 380

1200
aca gtg ttt ctg aag aca gta cta gag gaa aag caa gag gaa aga ttg
Thr Val Phe Leu Lys Thr Val Leu Glu Glu Lys Gln Glu Glu Arg Leu
385                 390                 395                 400

1248
acg tgg gag atg tcc tca act gct ctc cac ttg aag agc tat tac tgg
Thr Trp Glu Met Ser Ser Thr Ala Leu His Leu Lys Ser Tyr Tyr Trp
                405                 410                 415

1296
agg gtg caa agg tac ctt aaa ctc atg aag tac aac agc tac gcc tgg
Arg Val Gln Arg Tyr Leu Lys Leu Met Lys Tyr Asn Ser Tyr Ala Trp
            420                 425                 430

1344
atg gtg gtc cga gca gag atc ttc agg aac ttt ctc atc att cga aga
Met Val Val Arg Ala Glu Ile Phe Arg Asn Phe Leu Ile Ile Arg Arg
        435                 440                 445

1376
ctt acc aga aac ttc caa aac tga tctagacc
Leu Thr Arg Asn Phe Gln Asn
        450                 455

<210> SEQ ID NO 20
<211> LENGTH: 455
<212> TYPE: PRT
<213> ORGANISM: Artificial Sequence
<220> FEATURE:
<223> OTHER INFORMATION: LAP-mIFN    construct

<400> SEQUENCE: 20

Met Pro Pro Ser Gly Leu Arg Leu Leu Pro Leu Leu Pro Leu Leu
1               5                   10                  15

Trp Leu Leu Val Leu Thr Pro Gly Pro Pro Ala Ala Gly Leu Ser Thr
            20                  25                  30
```

```
Cys Lys Thr Ile Asp Met Glu Leu Val Lys Arg Lys Arg Ile Glu Ala
         35                  40                  45

Ile Arg Gly Gln Ile Leu Ser Lys Leu Arg Leu Ala Ser Pro Pro Ser
         50                  55                  60

Gln Gly Glu Val Pro Pro Gly Pro Leu Pro Ala Val Leu Ala Leu
 65                  70                  75                  80

Tyr Asn Ser Thr Arg Asp Arg Val Ala Gly Glu Ser Ala Glu Pro Glu
                 85                  90                  95

Pro Glu Pro Glu Ala Asp Tyr Tyr Ala Lys Glu Val Thr Arg Val Leu
             100                 105                 110

Met Val Glu Thr His Asn Glu Ile Tyr Asp Lys Phe Lys Gln Ser Thr
             115                 120                 125

His Ser Ile Tyr Met Phe Phe Asn Thr Ser Glu Leu Arg Glu Ala Val
         130                 135                 140

Pro Glu Pro Val Leu Leu Ser Arg Ala Glu Leu Arg Leu Leu Arg Arg
145                 150                 155                 160

Leu Lys Leu Lys Val Glu Gln His Val Glu Leu Tyr Gln Lys Tyr Ser
                 165                 170                 175

Asn Asn Ser Trp Arg Tyr Leu Ser Asn Arg Leu Leu Ala Pro Ser Asp
         180                 185                 190

Ser Pro Glu Trp Leu Ser Phe Asp Val Thr Gly Val Val Arg Gln Trp
         195                 200                 205

Leu Ser Arg Gly Gly Glu Ile Glu Gly Phe Arg Leu Ser Ala His Cys
210                 215                 220

Ser Cys Asp Ser Arg Asp Asn Thr Leu Gln Val Asp Ile Asn Gly Phe
225                 230                 235                 240

Thr Thr Gly Arg Arg Gly Asp Leu Ala Thr Ile His Gly Met Asn Arg
                 245                 250                 255

Pro Phe Leu Leu Leu Met Ala Thr Pro Leu Glu Arg Ala Gln His Leu
         260                 265                 270

Gln Ser Glu Phe Gly Gly Gly Ser Pro Leu Gly Leu Trp Ala Gly
         275                 280                 285

Gly Gly Ser Ala Ala Ala Ile Asn Tyr Lys Gln Leu Gln Leu Gln Glu
290                 295                 300

Arg Thr Asn Ile Arg Lys Cys Gln Glu Leu Leu Glu Gln Leu Asn Gly
305                 310                 315                 320

Lys Ile Asn Leu Thr Tyr Arg Ala Asp Phe Lys Ile Pro Met Glu Met
                 325                 330                 335

Thr Glu Lys Met Gln Lys Ser Tyr Thr Ala Phe Ala Ile Gln Glu Met
             340                 345                 350

Leu Gln Asn Val Phe Leu Val Phe Arg Asn Asn Phe Ser Ser Thr Gly
             355                 360                 365

Trp Asn Glu Thr Ile Val Val Arg Leu Leu Asp Glu Leu His Gln Gln
370                 375                 380

Thr Val Phe Leu Lys Thr Val Leu Glu Glu Lys Gln Glu Glu Arg Leu
385                 390                 395                 400

Thr Trp Glu Met Ser Ser Thr Ala Leu His Leu Lys Ser Tyr Tyr Trp
                 405                 410                 415

Arg Val Gln Arg Tyr Leu Lys Leu Met Lys Tyr Asn Ser Tyr Ala Trp
             420                 425                 430

Met Val Val Arg Ala Glu Ile Phe Arg Asn Phe Leu Ile Ile Arg Arg
             435                 440                 445

Leu Thr Arg Asn Phe Gln Asn
```

-continued

```
<210> SEQ ID NO 21
<211> LENGTH: 1352
<212> TYPE: DNA
<213> ORGANISM: Artificial Sequence
<220> FEATURE:
<223> OTHER INFORMATION: mIFNbeta-LAP construct
<221> NAME/KEY: CDS
<222> LOCATION: (1)..(1344)

<400> SEQUENCE: 21 atg aac aac agg tgg atc ctc cac gct gcg ttc ctg ctg tgc ttc tcc      48
Met Asn Asn Arg Trp Ile Leu His Ala Ala Phe Leu Leu Cys Phe Ser
 1               5                  10                  15 acc aca gcc ctc tcc atc aac tat aag cag ctc cag ctc caa gaa agg      96
Thr Thr Ala Leu Ser Ile Asn Tyr Lys Gln Leu Gln Leu Gln Glu Arg
             20                  25                  30 acg aac att cgg aaa tgt cag gag ctc ctg gag cag ctg aat gga aag     144
Thr Asn Ile Arg Lys Cys Gln Glu Leu Leu Glu Gln Leu Asn Gly Lys
         35                  40                  45 atc aac ctc acc tac agg gcg gac ttc aag atc cct atg gag atg acg     192
Ile Asn Leu Thr Tyr Arg Ala Asp Phe Lys Ile Pro Met Glu Met Thr
     50                  55                  60 gag aag atg cag aag agt tac act gcc ttt gcc atc caa gag atg ctc     240
Glu Lys Met Gln Lys Ser Tyr Thr Ala Phe Ala Ile Gln Glu Met Leu
 65                  70                  75                  80 cag aat gtc ttt ctt gtc ttc aga aac aat ttc tcc agc act ggg tgg     288
Gln Asn Val Phe Leu Val Phe Arg Asn Asn Phe Ser Ser Thr Gly Trp
                 85                  90                  95 aat gag act att gtt gta cgt ctc ctg gat gaa ctc cac cag cag aca     336
Asn Glu Thr Ile Val Val Arg Leu Leu Asp Glu Leu His Gln Gln Thr
            100                 105                 110 gtg ttt ctg aag aca gta cta gag gaa aag caa gag gaa aga ttg acg     384
Val Phe Leu Lys Thr Val Leu Glu Glu Lys Gln Glu Glu Arg Leu Thr
        115                 120                 125 tgg gag atg tcc tca act gct ctc cac ttg aag agc tat tac tgg agg     432
Trp Glu Met Ser Ser Thr Ala Leu His Leu Lys Ser Tyr Tyr Trp Arg
    130                 135                 140 gtg caa agg tac ctt aaa ctc atg aag tac aac agc tac gcc tgg atg     480
Val Gln Arg Tyr Leu Lys Leu Met Lys Tyr Asn Ser Tyr Ala Trp Met
145                 150                 155                 160 gtg gtc cga gca gag atc ttc agg aac ttt ctc atc att cga aga ctt     528
Val Val Arg Ala Glu Ile Phe Arg Asn Phe Leu Ile Ile Arg Arg Leu
                165                 170                 175 acc aga aac ttc caa aac gaa ttc ggg gga ggc gga tcc ccg ctc ggg     576
Thr Arg Asn Phe Gln Asn Glu Phe Gly Gly Gly Gly Ser Pro Leu Gly
            180                 185                 190 ctt tgg gcg gga ggg ggc tca gcg gcc gca cta tcc acc tgc aag act     624
Leu Trp Ala Gly Gly Gly Ser Ala Ala Ala Leu Ser Thr Cys Lys Thr
        195                 200                 205 atc gac atg gag ctg gtg aag cgg aag cgc atc gag gcc atc cgc ggc     672
Ile Asp Met Glu Leu Val Lys Arg Lys Arg Ile Glu Ala Ile Arg Gly
    210                 215                 220 cag atc ctg tcc aag ctg cgg ctc gcc agc ccc ccg agc cag ggg gag     720
Gln Ile Leu Ser Lys Leu Arg Leu Ala Ser Pro Pro Ser Gln Gly Glu
225                 230                 235                 240 gtg ccg ccc ggc ccg ctg ccc gag gcc gtg ctc gcc ctg tac aac agc     768
Val Pro Pro Gly Pro Leu Pro Glu Ala Val Leu Ala Leu Tyr Asn Ser
                245                 250                 255 acc cgc gac cgg gtg gcc ggg gag agt gca gaa ccg gag ccc gag cct     816
Thr Arg Asp Arg Val Ala Gly Glu Ser Ala Glu Pro Glu Pro Glu Pro
```

-continued

| | | |
|---|---|---|
| Thr Arg Asp Arg Val Ala Gly Glu Ser Ala Glu Pro Glu Pro Glu Pro<br>    260                    265                270 | | |
| gag gcc gac tac tac gcc aag gag gtc acc cgc gtg cta atg gtg aa<br>Glu Ala Asp Tyr Tyr Ala Lys Glu Val Thr Arg Val Leu Met Val Glu<br>    275                    280                285 | 864 | |
| acc cac aac gaa atc tat gac aag ttc aag cag agt aca cac agc ata<br>Thr His Asn Glu Ile Tyr Asp Lys Phe Lys Gln Ser Thr His Ser Ile<br>    290                    295                300 | 912 | |
| tat atg ttc ttc aac aca tca gag ctc cga gaa gcg gta cct gaa ccc<br>Tyr Met Phe Phe Asn Thr Ser Glu Leu Arg Glu Ala Val Pro Glu Pro<br>305                  310                315              320 | 960 | |
| gtg ttg ctc tcc cgg gca gag ctg cgt ctg ctg agg agg ctc aag tta<br>Val Leu Leu Ser Arg Ala Glu Leu Arg Leu Leu Arg Arg Leu Lys Leu<br>                325                330              335 | 1008 | |
| aaa gtg gag cag cac gtg gag ctg tac cag aaa tac agc aac aat tcc<br>Lys Val Glu Gln His Val Glu Leu Tyr Gln Lys Tyr Ser Asn Asn Ser<br>                    340                345              350 | 1056 | |
| tgg cga tac ctc agc aac cgg ctg ctg gca ccc agc gac tcg cca gag<br>Trp Arg Tyr Leu Ser Asn Arg Leu Leu Ala Pro Ser Asp Ser Pro Glu<br>                355                360              365 | 1104 | |
| tgg tta tct ttt gat gtc acc gga gtt gtg cgg cag tgg ttg agc cgt<br>Trp Leu Ser Phe Asp Val Thr Gly Val Val Arg Gln Trp Leu Ser Arg<br>    370                    375                380 | 1152 | |
| gga ggg gaa att gag ggc ttt cgc ctt agc gcc cac tgc tcc tgt gac<br>Gly Gly Glu Ile Glu Gly Phe Arg Leu Ser Ala His Cys Ser Cys Asp<br>385                  390              395              400 | 1200 | |
| agc agg gat aac aca ctg caa gtg gac atc aac ggg ttc act acc ggc<br>Ser Arg Asp Asn Thr Leu Gln Val Asp Ile Asn Gly Phe Thr Thr Gly<br>                    405                410              415 | 1248 | |
| cgc cga ggt gac ctg gcc acc att cat ggc atg aac cgg cct ttc ctg<br>Arg Arg Gly Asp Leu Ala Thr Ile His Gly Met Asn Arg Pro Phe Leu<br>                420                425              430 | 1296 | |
| ctt ctc atg gcc acc ccg ctg gag agg gcc cag cat ctg caa agc tga<br>Leu Leu Met Ala Thr Pro Leu Glu Arg Ala Gln His Leu Gln Ser<br>    435                    440                445 | 1344 | |
| tctagacc | 1352 | |

<210> SEQ ID NO 22
<211> LENGTH: 447
<212> TYPE: PRT
<213> ORGANISM: Artificial Sequence
<220> FEATURE:
<223> OTHER INFORMATION: mIFN -LAP construct

<400> SEQUENCE: 22

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

-continued

Val Phe Leu Lys Thr Val Leu Glu Glu Lys Gln Glu Glu Arg Leu Thr
            115                 120                 125

Trp Glu Met Ser Ser Thr Ala Leu His Leu Lys Ser Tyr Tyr Trp Arg
        130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn Glu Phe Gly Gly Gly Ser Pro Leu Gly
            180                 185                 190

Leu Trp Ala Gly Gly Ser Ala Ala Leu Ser Thr Cys Lys Thr
        195                 200                 205

Ile Asp Met Glu Leu Val Lys Arg Lys Arg Ile Glu Ala Ile Arg Gly
    210                 215                 220

Gln Ile Leu Ser Lys Leu Arg Leu Ala Ser Pro Ser Gln Gly Glu
225                 230                 235                 240

Val Pro Pro Gly Pro Leu Pro Glu Ala Val Leu Ala Leu Tyr Asn Ser
                245                 250                 255

Thr Arg Asp Arg Val Ala Gly Glu Ser Ala Glu Pro Glu Pro Glu Pro
            260                 265                 270

Glu Ala Asp Tyr Tyr Ala Lys Glu Val Thr Arg Val Leu Met Val Glu
        275                 280                 285

Thr His Asn Glu Ile Tyr Asp Lys Phe Lys Gln Ser Thr His Ser Ile
    290                 295                 300

Tyr Met Phe Phe Asn Thr Ser Glu Leu Arg Glu Ala Val Pro Glu Pro
305                 310                 315                 320

Val Leu Leu Ser Arg Ala Glu Leu Arg Leu Leu Arg Leu Lys Leu
                325                 330                 335

Lys Val Glu Gln His Val Glu Leu Tyr Gln Lys Tyr Ser Asn Asn Ser
            340                 345                 350

Trp Arg Tyr Leu Ser Asn Arg Leu Leu Ala Pro Ser Asp Ser Pro Glu
        355                 360                 365

Trp Leu Ser Phe Asp Val Thr Gly Val Val Arg Gln Trp Leu Ser Arg
    370                 375                 380

Gly Gly Glu Ile Glu Gly Phe Arg Leu Ser Ala His Cys Ser Cys Asp
385                 390                 395                 400

Ser Arg Asp Asn Thr Leu Gln Val Asp Ile Asn Gly Phe Thr Thr Gly
                405                 410                 415

Arg Arg Gly Asp Leu Ala Thr Ile His Gly Met Asn Arg Pro Phe Leu
            420                 425                 430

Leu Leu Met Ala Thr Pro Leu Glu Arg Ala Gln His Leu Gln Ser
        435                 440                 445

<210> SEQ ID NO 23
<211> LENGTH: 390
<212> TYPE: PRT
<213> ORGANISM: Homo sapiens

<400> SEQUENCE: 23

Met Pro Pro Ser Gly Leu Arg Leu Leu Pro Leu Leu Pro Leu Leu
1               5                   10                  15

Trp Leu Leu Val Leu Thr Pro Gly Pro Pro Ala Ala Gly Leu Ser Thr
            20                  25                  30

Cys Lys Thr Ile Asp Met Glu Leu Val Lys Arg Lys Arg Ile Glu Ala

```
                35                  40                  45
Ile Arg Gly Gln Ile Leu Ser Lys Leu Arg Leu Ala Ser Pro Pro Ser
 50                  55                  60
Gln Gly Glu Val Pro Pro Gly Pro Leu Pro Glu Ala Val Leu Ala Leu
 65                  70                  75                  80
Tyr Asn Ser Thr Arg Asp Arg Val Ala Gly Glu Ser Ala Glu Pro Glu
                 85                  90                  95
Pro Glu Pro Glu Ala Asp Tyr Tyr Ala Lys Glu Val Thr Arg Val Leu
                100                 105                 110
Met Val Glu Thr His His Glu Ile Tyr Asp Lys Phe Lys Gln Ser Thr
                115                 120                 125
His Ser Thr Tyr Met Phe Phe Asn Ile Ser Glu Leu Arg Glu Ala Val
130                 135                 140
Pro Glu Pro Val Leu Leu Ser Arg Ala Glu Leu Arg Leu Leu Arg Leu
145                 150                 155                 160
Lys Leu Lys Val Glu Gln His Val Glu Leu Tyr Gln Lys Tyr Ser Asn
                165                 170                 175
Asn Ser Trp Arg Tyr Leu Ser Asn Arg Leu Leu Ala Pro Ser Asp Ser
                180                 185                 190
Pro Glu Trp Leu Ser Phe Asp Val Thr Gly Val Val Arg Gln Trp Leu
                195                 200                 205
Ser Arg Gly Gly Glu Ile Glu Gly Phe Arg Leu Ser Ala His Cys Ser
210                 215                 220
Cys Asp Ser Arg Asp Asn Thr Leu Gln Val Asp Ile Asn Gly Phe Thr
225                 230                 235                 240
Thr Gly Arg Arg Gly Asp Leu Ala Thr Ile His Gly Met Asn Arg Pro
                245                 250                 255
Phe Leu Leu Leu Met Ala Thr Pro Leu Glu Arg Ala Gln His Leu Gln
                260                 265                 270
Ser Ser Arg His Arg Arg Ala Leu Asp Thr Asn Tyr Cys Phe Ser Ser
                275                 280                 285
Thr Glu Lys Asn Cys Cys Val Arg Gln Leu Tyr Ile Asp Phe Arg Lys
290                 295                 300
Asp Leu Gly Trp Lys Trp Ile His Glu Pro Lys Gly Tyr His Ala Asn
305                 310                 315                 320
Phe Cys Leu Gly Pro Cys Pro Tyr Ile Trp Ser Leu Asp Thr Gln Tyr
                325                 330                 335
Ser Lys Val Leu Ala Leu Tyr Asn Gln His Asn Pro Gly Ala Ser Ala
                340                 345                 350
Ala Pro Cys Cys Val Pro Gln Ala Leu Glu Pro Leu Pro Ile Val Tyr
                355                 360                 365
Tyr Val Gly Arg Lys Pro Lys Val Glu Gln Leu Ser Asn Met Ile Val
370                 375                 380
Arg Ser Cys Lys Cys Ser
385                 390

<210> SEQ ID NO 24
<211> LENGTH: 414
<212> TYPE: PRT
<213> ORGANISM: Homo sapiens

<400> SEQUENCE: 24

Met His Tyr Cys Val Leu Ser Ala Phe Leu Ile Leu His Leu Val Thr
 1               5                  10                  15
```

-continued

```
Val Ala Leu Ser Leu Ser Thr Cys Ser Thr Leu Asp Met Gln Gln Phe
             20                  25                  30
Met Arg Lys Arg Ile Glu Ala Ile Arg Gly Gln Ile Leu Ser Lys Leu
         35                  40                  45
Lys Leu Thr Ser Pro Pro Glu Asp Tyr Pro Glu Pro Glu Glu Val Pro
     50                  55                  60
Pro Glu Val Ile Ser Ile Tyr Asn Ser Thr Arg Asp Leu Leu Gln Glu
 65                  70                  75                  80
Lys Ala Ser Arg Arg Ala Ala Cys Glu Arg Glu Arg Ser Asp Glu
                 85                  90                  95
Glu Tyr Tyr Ala Lys Glu Val Tyr Lys Ile Asp Met Pro Pro Phe Phe
             100                 105                 110
Pro Ser Glu Asn Ala Ile Pro Pro Thr Phe Tyr Arg Pro Tyr Phe Arg
         115                 120                 125
Ile Val Arg Phe Asp Val Ser Ala Met Glu Lys Asn Ala Ser Asn Leu
 130                 135                 140
Val Lys Ala Glu Phe Arg Val Phe Arg Leu Gln Asn Pro Lys Ala Arg
145                 150                 155                 160
Val Pro Glu Gln Arg Ile Glu Leu Tyr Gln Ile Leu Lys Ser Lys Asp
                 165                 170                 175
Leu Ile Ser Pro Thr Gln Arg Tyr Ile Asp Ser Lys Val Val Lys Thr
             180                 185                 190
Arg Ala Glu Gly Glu Trp Leu Ser Phe Asp Val Thr Asp Ala Val His
         195                 200                 205
Glu Trp Leu His His Lys Asp Arg Asn Leu Gly Phe Lys Ile Ser Leu
 210                 215                 220
His Cys Pro Cys Cys Thr Phe Val Pro Ser Asn Asn Tyr Ile Ile Pro
225                 230                 235                 240
Asn Lys Ser Glu Glu Leu Glu Ala Arg Phe Ala Gly Ile Asp Gly Ile
                 245                 250                 255
Ser Thr Tyr Thr Ser Gly Asp Gln Lys Thr Ile Lys Ser Thr Arg Lys
             260                 265                 270
Lys Asn Ser Gly Lys Thr Pro His Leu Leu Leu Met Leu Leu Pro Ser
         275                 280                 285
Tyr Arg Leu Glu Ser Gln Gln Thr Asn Arg Arg Lys Lys Arg Ala Leu
 290                 295                 300
Asp Ala Ala Tyr Cys Phe Arg Asn Val Gln Asp Asn Cys Cys Leu Arg
305                 310                 315                 320
Pro Leu Tyr Ile Asp Phe Lys Arg Asp Leu Gly Trp Lys Trp Ile His
                 325                 330                 335
Glu Pro Lys Gly Tyr Asn Ala Asn Phe Cys Ala Gly Ala Cys Pro Tyr
             340                 345                 350
Leu Trp Ser Ser Asp Thr Gln His Ser Arg Val Leu Ser Leu Tyr Asn
         355                 360                 365
Thr Glu Asn Pro Glu Ala Ser Ala Ser Pro Cys Cys Val Ser Gln Asp
 370                 375                 380
Leu Glu Pro Leu Thr Ile Leu Tyr Tyr Ile Gly Lys Ile Pro Lys Ile
385                 390                 395                 400
Glu Gln Leu Ser Asn Met Ile Val Lys Ser Cys Lys Cys Ser
                 405                 410
```

<210> SEQ ID NO 25
<211> LENGTH: 412
<212> TYPE: PRT

-continued

<213> ORGANISM: Homo sapiens

<400> SEQUENCE: 25

```
Met Lys Met His Leu Gln Arg Ala Leu Val Val Leu Ala Leu Leu His
1               5                   10                  15

Phe Ala Thr Val Ser Leu Ser Leu Ser Thr Cys Thr Thr Leu Asp Phe
                20                  25                  30

Gly His Ile Lys Lys Arg Val Glu Ala Ile Arg Gly Gln Ile Leu
                35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu His Gly Glu Arg Lys Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
                115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
                180                 185                 190

Thr Arg Gly Thr Ala Glu Trp Leu Ser Phe Asp Val Thr Asp Thr Val
                195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
                260                 265                 270

Asn Asn Asn Pro His Leu Ile Leu Met Met Ile Pro Pro His Arg Leu
                275                 280                 285

Asp Asn Pro Gly Gln Gly Gly Gln Arg Lys Lys Arg Ala Leu Asp Ile
290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
    355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400
```

```
Leu Ser Asn Met Val Val Lys Ser Cys Lys Cys Ser
            405             410
```

<210> SEQ ID NO 26
<211> LENGTH: 304
<212> TYPE: PRT
<213> ORGANISM: Gallus domesticus

<400> SEQUENCE: 26

```
Met Asp Pro Met Ser Ile Gly Pro Lys Ser Cys Gly Gly Ser Pro Trp
1               5                   10                  15

Arg Pro Pro Gly Thr Ala Pro Trp Ser Ile Gly Ser Arg Arg Ala Thr
            20                  25                  30

Ala Ser Ser Cys Ser Thr Ser Ser Arg Val Arg Ala Glu Val Gly
        35                  40                  45

Gly Arg Ala Leu Leu His Arg Ala Glu Leu Arg Met Leu Arg Gln Lys
    50                  55                  60

Ala Ala Ala Asp Ser Ala Gly Thr Glu Gln Arg Leu Glu Leu Tyr Gln
65                  70                  75                  80

Gly Tyr Gly Asn Ala Ser Trp Arg Tyr Leu His Gly Arg Ser Val Arg
                85                  90                  95

Ala Thr Ala Asp Asp Glu Trp Leu Ser Phe Asp Val Thr Asp Ala Val
            100                 105                 110

His Gln Trp Leu Ser Gly Ser Glu Leu Leu Gly Val Phe Lys Leu Ser
        115                 120                 125

Val His Cys Pro Cys Glu Met Gly Pro Gly His Ala Asp Glu Met Arg
    130                 135                 140

Ile Ser Ile Glu Gly Phe Glu Gln Gln Arg Gly Asp Met Gln Ser Ile
145                 150                 155                 160

Ala Lys Lys His Arg Arg Val Pro Tyr Val Leu Ala Met Ala Leu Pro
                165                 170                 175

Ala Glu Arg Ala Asn Glu Leu His Ser Ala Arg Arg Arg Arg Asp Leu
            180                 185                 190

Asp Thr Asp Tyr Cys Phe Gly Pro Gly Thr Asp Glu Lys Asn Cys Cys
        195                 200                 205

Val Arg Pro Leu Tyr Ile Asp Phe Arg Lys Asp Leu Gln Trp Lys Trp
    210                 215                 220

Ile His Glu Pro Lys Gly Tyr Met Ala Asn Phe Cys Met Gly Pro Cys
225                 230                 235                 240

Pro Tyr Ile Trp Ser Ala Asp Thr Gln Tyr Ile Lys Val Leu Ala Leu
                245                 250                 255

Tyr Asn Gln Asn Asn Pro Gly Ala Ser Ala Ala Pro Cys Cys Val Pro
            260                 265                 270

Gln Ile Leu Asp Pro Leu Pro Ile Ile Tyr Tyr Val Gly Arg Asn Val
        275                 280                 285

Arg Val Glu Gln Leu Ser Asn Met Val Val Arg Ala Cys Lys Cys Ser
    290                 295                 300
```

<210> SEQ ID NO 27
<211> LENGTH: 383
<212> TYPE: PRT
<213> ORGANISM: Rana sp.

<400> SEQUENCE: 27

```
Met Glu Val Leu Trp Met Leu Leu Val Leu Val Leu His Leu Ser
1               5                   10                  15
```

-continued

```
Ser Leu Ala Met Ser Leu Ser Thr Cys Lys Ala Val Asp Met Glu Glu
         20                  25                  30

Val Arg Lys Arg Arg Ile Glu Ala Ile Arg Gly Gln Ile Leu Ser Lys
         35                  40                  45

Leu Lys Leu Asp Lys Ile Pro Asp Val Asp Ser Glu Lys Met Thr Val
 50                  55                  60

Pro Ser Glu Ala Ile Phe Leu Tyr Asn Ser Thr Leu Glu Val Ile Arg
 65                  70                  75                  80

Glu Lys Ala Thr Arg Glu Glu Glu His Val Gly His Asp Gln Asn
                 85                  90                  95

Ile Gln Asp Tyr Tyr Ala Lys Gln Val Tyr Arg Phe Glu Ser Ile Thr
                100                 105                 110

Glu Leu Glu Asp His Glu Phe Lys Phe Lys Phe Asn Ala Ser Asn Val
            115                 120                 125

Arg Glu Asn Val Gly Met Asn Ser Leu Leu His His Ala Glu Leu Arg
130                 135                 140

Met Tyr Lys Lys Gln Thr Asp Lys Asn Met Asp Gln Arg Met Glu Leu
145                 150                 155                 160

Phe Trp Lys Tyr Gln Glu Asn Gly Thr Thr His Ser Arg Tyr Leu Glu
                165                 170                 175

Ser Lys Tyr Ile Thr Pro Val Thr Asp Asp Glu Trp Met Ser Phe Asp
            180                 185                 190

Val Thr Lys Thr Val Asn Glu Trp Leu Lys Arg Ala Glu Glu Asn Glu
            195                 200                 205

Gln Phe Gly Leu Gln Pro Ala Cys Lys Cys Pro Thr Pro Gln Ala Lys
        210                 215                 220

Asp Ile Asp Ile Glu Gly Phe Pro Ala Leu Arg Gly Asp Leu Ala Ser
225                 230                 235                 240

Leu Ser Ser Lys Glu Asn Thr Lys Pro Tyr Leu Met Ile Thr Ser His
                245                 250                 255

Pro Ala Glu Arg Ile Asp Thr Val Thr Ser Ser Arg Lys Lys Arg Gly
            260                 265                 270

Val Gly Gln Glu Tyr Cys Phe Gly Asn Asn Gly Pro Asn Cys Cys Val
        275                 280                 285

Lys Pro Leu Tyr Ile Asn Phe Arg Lys Asp Leu Gly Trp Lys Trp Ile
    290                 295                 300

His Glu Pro Lys Gly Tyr Glu Ala Asn Tyr Cys Leu Gly Asn Cys Pro
305                 310                 315                 320

Tyr Ile Trp Ser Met Asp Thr Gln Tyr Ser Lys Val Leu Ser Leu Tyr
                325                 330                 335

Asn Gln Asn Asn Pro Gly Ala Ser Ile Ser Pro Cys Cys Val Pro Asp
            340                 345                 350

Val Leu Glu Pro Leu Pro Ile Ile Tyr Tyr Val Gly Arg Ile Ala Lys
        355                 360                 365

Val Glu Gln Leu Ser Asn Met Val Val Arg Ser Cys Asn Cys Ser
    370                 375                 380
```

<210> SEQ ID NO 28
<211> LENGTH: 8
<212> TYPE: PRT
<213> ORGANISM: Homo sapiens

<400> SEQUENCE: 28

```
Ala Pro Gln Gly Ile Ala Gly Gln
 1               5
```

```
<210> SEQ ID NO 29
<211> LENGTH: 8
<212> TYPE: PRT
<213> ORGANISM: Homo sapiens

<400> SEQUENCE: 29

Gly Pro Gln Gly Leu Leu Gly Ala
1               5

<210> SEQ ID NO 30
<211> LENGTH: 8
<212> TYPE: PRT
<213> ORGANISM: Homo sapiens

<400> SEQUENCE: 30

Gly Pro Gln Gly Leu Ala Gly Gln
1               5

<210> SEQ ID NO 31
<211> LENGTH: 8
<212> TYPE: PRT
<213> ORGANISM: Homo sapiens

<400> SEQUENCE: 31

Gly Pro Leu Gly Ile Ala Gly Ile
1               5

<210> SEQ ID NO 32
<211> LENGTH: 8
<212> TYPE: PRT
<213> ORGANISM: Homo sapiens

<400> SEQUENCE: 32

Gly Pro Glu Gly Leu Arg Val Gly
1               5

<210> SEQ ID NO 33
<211> LENGTH: 8
<212> TYPE: PRT
<213> ORGANISM: Rattus sp.

<400> SEQUENCE: 33

Ala Ala Tyr His Leu Val Ser Gln
1               5

<210> SEQ ID NO 34
<211> LENGTH: 8
<212> TYPE: PRT
<213> ORGANISM: Rattus sp.

<400> SEQUENCE: 34

Met Asp Ala Phe Leu Glu Ser Ser
1               5

<210> SEQ ID NO 35
<211> LENGTH: 8
<212> TYPE: PRT
<213> ORGANISM: Rattus sp.

<400> SEQUENCE: 35

Glu Pro Gln Ala Leu Ala Met Ser
1               5
```

```
<210> SEQ ID NO 36
<211> LENGTH: 8
<212> TYPE: PRT
<213> ORGANISM: Rattus sp.

<400> SEQUENCE: 36

Gln Ala Leu Ala Met Ser Ala Ile
1               5

<210> SEQ ID NO 37
<211> LENGTH: 8
<212> TYPE: PRT
<213> ORGANISM: Gallus domesticus

<400> SEQUENCE: 37

Pro Ser Tyr Phe Leu Asn Ala Gly
1               5

<210> SEQ ID NO 38
<211> LENGTH: 8
<212> TYPE: PRT
<213> ORGANISM: Homo sapiens

<400> SEQUENCE: 38

Tyr Glu Ala Gly Leu Gly Val Val
1               5

<210> SEQ ID NO 39
<211> LENGTH: 8
<212> TYPE: PRT
<213> ORGANISM: Homo sapiens

<400> SEQUENCE: 39

Ala Gly Leu Gly Val Val Glu Arg
1               5

<210> SEQ ID NO 40
<211> LENGTH: 8
<212> TYPE: PRT
<213> ORGANISM: Homo sapiens

<400> SEQUENCE: 40

Ala Gly Leu Gly Ile Ser Ser Thr
1               5

<210> SEQ ID NO 41
<211> LENGTH: 8
<212> TYPE: PRT
<213> ORGANISM: Unknown
<220> FEATURE:
<223> OTHER INFORMATION: Sequence source uncertain

<400> SEQUENCE: 41

Gly Ala Met Phe Leu Glu Ala Ile
1               5

<210> SEQ ID NO 42
<211> LENGTH: 8
<212> TYPE: PRT
<213> ORGANISM: Homo sapiens

<400> SEQUENCE: 42

Ile Pro Glu Asn Phe Phe Gly Val
1               5
```

```
<210> SEQ ID NO 43
<211> LENGTH: 8
<212> TYPE: PRT
<213> ORGANISM: Homo sapiens

<400> SEQUENCE: 43

Thr Glu Gly Glu Ala Arg Gly Ser
1               5

<210> SEQ ID NO 44
<211> LENGTH: 8
<212> TYPE: PRT
<213> ORGANISM: Homo sapiens

<400> SEQUENCE: 44

Arg Ala Ile His Ile Gln Ala Glu
1               5

<210> SEQ ID NO 45
<211> LENGTH: 8
<212> TYPE: PRT
<213> ORGANISM: Homo sapiens

<400> SEQUENCE: 45

Leu Arg Ala Tyr Leu Leu Pro Ala
1               5

<210> SEQ ID NO 46
<211> LENGTH: 8
<212> TYPE: PRT
<213> ORGANISM: Cavia porcellus
<220> FEATURE:
<221> NAME/KEY: SITE
<222> LOCATION: (3)..(3)
<223> OTHER INFORMATION: Xaa=Hyp

<400> SEQUENCE: 46

Gly Ala Xaa Gly Leu Glx Gly His
1               5

<210> SEQ ID NO 47
<211> LENGTH: 8
<212> TYPE: PRT
<213> ORGANISM: Rattus sp.

<400> SEQUENCE: 47

Gly Pro Gln Gly Val Arg Gly Glu
1               5

<210> SEQ ID NO 48
<211> LENGTH: 8
<212> TYPE: PRT
<213> ORGANISM: Rattus sp.

<400> SEQUENCE: 48

Gly Pro Ala Gly Val Gln Gly Pro
1               5

<210> SEQ ID NO 49
<211> LENGTH: 8
<212> TYPE: PRT
<213> ORGANISM: Rattus sp.
<220> FEATURE:
<221> NAME/KEY: SITE
<222> LOCATION: (6)..(6)
<223> OTHER INFORMATION: Xaa=Hyp
```

```
<400> SEQUENCE: 49

Gly Pro Ser Gly Leu Xaa Gly Pro
1               5

<210> SEQ ID NO 50
<211> LENGTH: 8
<212> TYPE: PRT
<213> ORGANISM: Rattus sp.

<400> SEQUENCE: 50

Gly Pro Ala Gly Glu Arg Gly Ser
1               5

<210> SEQ ID NO 51
<211> LENGTH: 8
<212> TYPE: PRT
<213> ORGANISM: Rattus sp.

<400> SEQUENCE: 51

Gly Ala Lys Gly Leu Thr Gly Ser
1               5

<210> SEQ ID NO 52
<211> LENGTH: 8
<212> TYPE: PRT
<213> ORGANISM: Rattus sp.

<400> SEQUENCE: 52

Gly Pro Ala Gly Gln Asp Gly Pro
1               5

<210> SEQ ID NO 53
<211> LENGTH: 8
<212> TYPE: PRT
<213> ORGANISM: Rattus sp.

<400> SEQUENCE: 53

Gly Pro Ala Gly Phe Ala Gly Pro
1               5

<210> SEQ ID NO 54
<211> LENGTH: 8
<212> TYPE: PRT
<213> ORGANISM: Rattus sp.

<400> SEQUENCE: 54

Gly Pro Ile Gly Asn Val Gly Ala
1               5

<210> SEQ ID NO 55
<211> LENGTH: 8
<212> TYPE: PRT
<213> ORGANISM: Rattus sp.
<220> FEATURE:
<221> NAME/KEY: SITE
<222> LOCATION: (3)..(3)
<223> OTHER INFORMATION: Xaa=Hyl

<400> SEQUENCE: 55

Gly Pro Xaa Gly Ser Arg Gly Ala
1               5

<210> SEQ ID NO 56
<211> LENGTH: 8
<212> TYPE: PRT
```

```
<213> ORGANISM: Bos taurus

<400> SEQUENCE: 56

Gly Pro Gln Gly Ile Ala Gly Gln
1               5

<210> SEQ ID NO 57
<211> LENGTH: 8
<212> TYPE: PRT
<213> ORGANISM: Bos taurus

<400> SEQUENCE: 57

Gly Pro Gln Gly Leu Leu Gly Ala
1               5

<210> SEQ ID NO 58
<211> LENGTH: 8
<212> TYPE: PRT
<213> ORGANISM: Homo sapiens

<400> SEQUENCE: 58

Ile Pro Glu Asn Phe Phe Gly Val
1               5

<210> SEQ ID NO 59
<211> LENGTH: 8
<212> TYPE: PRT
<213> ORGANISM: Homo sapiens

<400> SEQUENCE: 59

Pro Pro Gly Ala Tyr His Gly Ala
1               5

<210> SEQ ID NO 60
<211> LENGTH: 8
<212> TYPE: PRT
<213> ORGANISM: Homo sapiens

<400> SEQUENCE: 60

Arg Ala Ile His Ile Gln Ala Glu
1               5

<210> SEQ ID NO 61
<211> LENGTH: 8
<212> TYPE: PRT
<213> ORGANISM: Homo sapiens

<400> SEQUENCE: 61

Gly Pro His Leu Leu Val Glu Ala
1               5

<210> SEQ ID NO 62
<211> LENGTH: 8
<212> TYPE: PRT
<213> ORGANISM: Homo sapiens

<400> SEQUENCE: 62

Leu Arg Ala Tyr Leu Leu Pro Ala
1               5

<210> SEQ ID NO 63
<211> LENGTH: 8
<212> TYPE: PRT
<213> ORGANISM: Homo sapiens
```

```
<400> SEQUENCE: 63

Gly Pro Glu Gly Leu Arg Val Gly
1               5

<210> SEQ ID NO 64
<211> LENGTH: 8
<212> TYPE: PRT
<213> ORGANISM: Homo sapiens

<400> SEQUENCE: 64

Arg Val Gly Phe Tyr Glu Ser Asp
1               5

<210> SEQ ID NO 65
<211> LENGTH: 8
<212> TYPE: PRT
<213> ORGANISM: Homo sapiens

<400> SEQUENCE: 65

Leu Leu Ser Ala Leu Val Glu Thr
1               5

<210> SEQ ID NO 66
<211> LENGTH: 8
<212> TYPE: PRT
<213> ORGANISM: Unknown
<220> FEATURE:
<223> OTHER INFORMATION: Sequence source uncertain

<400> SEQUENCE: 66

Glu Ala Ile Pro Met Ser Ile Pro
1               5

<210> SEQ ID NO 67
<211> LENGTH: 8
<212> TYPE: PRT
<213> ORGANISM: Unknown
<220> FEATURE:
<223> OTHER INFORMATION: Sequence source uncertain

<400> SEQUENCE: 67

Ile Ala Gly Arg Ser Leu Asn Pro
1               5

<210> SEQ ID NO 68
<211> LENGTH: 8
<212> TYPE: PRT
<213> ORGANISM: Gallus domesticus

<400> SEQUENCE: 68

Leu Asn Ala Gly Phe Thr Ala Ser
1               5

<210> SEQ ID NO 69
<211> LENGTH: 8
<212> TYPE: PRT
<213> ORGANISM: Homo sapiens

<400> SEQUENCE: 69

Ile Pro Glu Asn Phe Phe Gly Val
1               5

<210> SEQ ID NO 70
<211> LENGTH: 8
<212> TYPE: PRT
```

```
<213> ORGANISM: Unknown
<220> FEATURE:
<223> OTHER INFORMATION: Sequence source uncertain

<400> SEQUENCE: 70

Lys Pro Gln Gln Phe Phe Gly Leu
1               5

<210> SEQ ID NO 71
<211> LENGTH: 8
<212> TYPE: PRT
<213> ORGANISM: Homo sapiens

<400> SEQUENCE: 71

Asp Val Ala Gln Phe Val Leu Thr
1               5

<210> SEQ ID NO 72
<211> LENGTH: 8
<212> TYPE: PRT
<213> ORGANISM: Homo sapiens

<400> SEQUENCE: 72

Asp Thr Leu Glu Val Met Arg Lys
1               5

<210> SEQ ID NO 73
<211> LENGTH: 8
<212> TYPE: PRT
<213> ORGANISM: Homo sapiens

<400> SEQUENCE: 73

Asp Val Gly His Phe Arg Thr Phe
1               5

<210> SEQ ID NO 74
<211> LENGTH: 8
<212> TYPE: PRT
<213> ORGANISM: Homo sapiens

<400> SEQUENCE: 74

Asp Ser Gly Gly Phe Met Leu Thr
1               5

<210> SEQ ID NO 75
<211> LENGTH: 8
<212> TYPE: PRT
<213> ORGANISM: Homo sapiens

<400> SEQUENCE: 75

Arg Val Ala Glu Met Arg Gly Glu
1               5

<210> SEQ ID NO 76
<211> LENGTH: 8
<212> TYPE: PRT
<213> ORGANISM: Homo sapiens

<400> SEQUENCE: 76

Asp Leu Gly Arg Phe Gln Thr Phe
1               5

<210> SEQ ID NO 77
<211> LENGTH: 8
<212> TYPE: PRT
```

<213> ORGANISM: Homo sapiens

<400> SEQUENCE: 77

Pro Phe Ser Pro Leu Val Ala Thr
1               5

<210> SEQ ID NO 78
<211> LENGTH: 8
<212> TYPE: PRT
<213> ORGANISM: Homo sapiens

<400> SEQUENCE: 78

Leu Arg Ala Tyr Leu Leu Pro Ala
1               5

<210> SEQ ID NO 79
<211> LENGTH: 8
<212> TYPE: PRT
<213> ORGANISM: Unknown
<220> FEATURE:
<223> OTHER INFORMATION: Sequence source uncertain

<400> SEQUENCE: 79

Ala Pro Gly Asn Ala Ser Glu Ser
1               5

<210> SEQ ID NO 80
<211> LENGTH: 8
<212> TYPE: PRT
<213> ORGANISM: Unknown
<220> FEATURE:
<223> OTHER INFORMATION: Sequence source uncertain

<400> SEQUENCE: 80

Phe Ser Ser Glu Ser Lys Arg Glu
1               5

<210> SEQ ID NO 81
<211> LENGTH: 8
<212> TYPE: PRT
<213> ORGANISM: Bos taurus

<400> SEQUENCE: 81

Ala Gly Gly Ala Gln Met Gly Val
1               5

<210> SEQ ID NO 82
<211> LENGTH: 8
<212> TYPE: PRT
<213> ORGANISM: Bos taurus

<400> SEQUENCE: 82

Gln Met Gly Val Met Gln Gly Pro
1               5

<210> SEQ ID NO 83
<211> LENGTH: 8
<212> TYPE: PRT
<213> ORGANISM: Bos taurus

<400> SEQUENCE: 83

Met Ala Ala Ser Leu Lys Arg Pro
1               5

<210> SEQ ID NO 84

```
<211> LENGTH: 8
<212> TYPE: PRT
<213> ORGANISM: Bos taurus

<400> SEQUENCE: 84

Met Ala Ala Ser Ala Lys Arg Glu
1               5

<210> SEQ ID NO 85
<211> LENGTH: 8
<212> TYPE: PRT
<213> ORGANISM: Bos taurus

<400> SEQUENCE: 85

Met Ala Ala Ser Leu Arg Lys Pro
1               5

<210> SEQ ID NO 86
<211> LENGTH: 8
<212> TYPE: PRT
<213> ORGANISM: Bos taurus

<400> SEQUENCE: 86

Gln Ala Gln Ala Ile Leu Gln Gln
1               5

<210> SEQ ID NO 87
<211> LENGTH: 8
<212> TYPE: PRT
<213> ORGANISM: Homo sapiens

<400> SEQUENCE: 87

Arg Ala Ile His Ile Gln Ala Glu
1               5

<210> SEQ ID NO 88
<211> LENGTH: 8
<212> TYPE: PRT
<213> ORGANISM: Bos taurus

<400> SEQUENCE: 88

Leu Val Glu Ala Leu Tyr Leu Val
1               5

<210> SEQ ID NO 89
<211> LENGTH: 8
<212> TYPE: PRT
<213> ORGANISM: Bos taurus

<400> SEQUENCE: 89

Glu Ala Leu Tyr Leu Val Cys Gly
1               5

<210> SEQ ID NO 90
<211> LENGTH: 8
<212> TYPE: PRT
<213> ORGANISM: Homo sapiens

<400> SEQUENCE: 90

Ile Pro Glu Asn Phe Phe Gly Val
1               5

<210> SEQ ID NO 91
<211> LENGTH: 8
<212> TYPE: PRT
```

<213> ORGANISM: Homo sapiens

<400> SEQUENCE: 91

Gly Pro His Leu Leu Val Glu Ala
1               5

<210> SEQ ID NO 92
<211> LENGTH: 8
<212> TYPE: PRT
<213> ORGANISM: Homo sapiens

<400> SEQUENCE: 92

Pro Pro Glu Glu Leu Lys Phe Gln
1               5

<210> SEQ ID NO 93
<211> LENGTH: 8
<212> TYPE: PRT
<213> ORGANISM: Homo sapiens

<400> SEQUENCE: 93

Gly Pro Pro Gly Val Val Gly Pro
1               5

<210> SEQ ID NO 94
<211> LENGTH: 8
<212> TYPE: PRT
<213> ORGANISM: Homo sapiens

<400> SEQUENCE: 94

Gly Pro Pro Gly Leu Arg Gly Glu
1               5

<210> SEQ ID NO 95
<211> LENGTH: 8
<212> TYPE: PRT
<213> ORGANISM: Homo sapiens

<400> SEQUENCE: 95

Gly Pro Glu Gly Val Val Gly Pro
1               5

<210> SEQ ID NO 96
<211> LENGTH: 8
<212> TYPE: PRT
<213> ORGANISM: Homo sapiens

<400> SEQUENCE: 96

Ile Pro Glu Asn Phe Phe Gly Val
1               5

<210> SEQ ID NO 97
<211> LENGTH: 8
<212> TYPE: PRT
<213> ORGANISM: Homo sapiens

<400> SEQUENCE: 97

Pro Pro Gly Ala Tyr His Gly Ala
1               5

<210> SEQ ID NO 98
<211> LENGTH: 8
<212> TYPE: PRT
<213> ORGANISM: Homo sapiens

```
<400> SEQUENCE: 98

Arg Ala Ile His Ile Gln Ala Glu
1               5

<210> SEQ ID NO 99
<211> LENGTH: 8
<212> TYPE: PRT
<213> ORGANISM: Homo sapiens

<400> SEQUENCE: 99

Arg Ala Ile His Ile Gln Ala Glu
1               5

<210> SEQ ID NO 100
<211> LENGTH: 8
<212> TYPE: PRT
<213> ORGANISM: Homo sapiens

<400> SEQUENCE: 100

Gly Pro His Leu Leu Val Glu Ala
1               5
```